US009688990B2

(12) United States Patent
Taulan-Cadars

(10) Patent No.: US 9,688,990 B2
(45) Date of Patent: Jun. 27, 2017

(54) METHODS AND PHARMACEUTICAL COMPOSITIONS FOR TREATMENT OF CYSTIC FIBROSIS

(71) Applicants: INSERM (INSTITUT NATIONAL DE LA SANTE ET DE LA RECHERCHE MEDICALE), Paris (FR); UNIVERSITE DE MONTPELLIER, Montpelleir (FR)

(72) Inventor: Magali Taulan-Cadars, Montpellier (FR)

(73) Assignees: Institut National de la Sante et de la Recherche Medicale (INSERM), Paris (FR); Universite de Montpellier, Montpellier (FR)

( * ) Notice: Subject to any disclaimer, the term of this patent is extended or adjusted under 35 U.S.C. 154(b) by 0 days.

(21) Appl. No.: 15/021,137

(22) PCT Filed: Sep. 12, 2014

(86) PCT No.: PCT/EP2014/069522
§ 371 (c)(1),
(2) Date: Mar. 10, 2016

(87) PCT Pub. No.: WO2015/036552
PCT Pub. Date: Mar. 19, 2015

(65) Prior Publication Data
US 2016/0222390 A1    Aug. 4, 2016

(30) Foreign Application Priority Data

Sep. 12, 2013    (EP) .................................... 13306250

(51) Int. Cl.
| A61K 48/00 | (2006.01) |
| C12N 15/113 | (2010.01) |
| A61K 45/06 | (2006.01) |
| A61K 31/404 | (2006.01) |
| A61K 31/443 | (2006.01) |
| A61K 31/47 | (2006.01) |
| A61K 31/711 | (2006.01) |
| A61K 31/713 | (2006.01) |
| A61K 31/7105 | (2006.01) |

(52) U.S. Cl.
CPC ........ *C12N 15/1138* (2013.01); *A61K 31/404* (2013.01); *A61K 31/443* (2013.01); *A61K 31/47* (2013.01); *A61K 31/711* (2013.01); *A61K 31/713* (2013.01); *A61K 31/7105* (2013.01); *A61K 45/06* (2013.01); *C12N 2310/11* (2013.01); *C12N 2310/113* (2013.01); *C12N 2310/3231* (2013.01); *C12N 2320/31* (2013.01); *C12N 2320/33* (2013.01)

(58) Field of Classification Search
CPC ...................................................... C07H 21/04
See application file for complete search history.

(56) References Cited

FOREIGN PATENT DOCUMENTS

WO    2008/074328 A2    6/2008
WO    2012/049665 A1    4/2012

OTHER PUBLICATIONS

Naruse et al. (Best Practice & Res Clin Gastroenterology 2002: vol. 16:511-516).*
Friedman et al., "Correction of aberrant splicing of the cystic fibrosis transmembrane conductance regulator (CFTR) gene by antisense oligonucleotides", Journal of Biological Chemistry, Dec. 17, 1999, pp. 36193-36199, vol. 274, No. 51.
Megiorni et al., "Synergistic Post-Transcriptional Regulation of the Cystic Fibrosis Transmembrane Conductance Regulator (CFTR) by miR-101 and miR-494 Specific Binding", Plos One, Oct. 20, 2011, p. e26601, vol. 6, No. 10.
Gillen et al., "microRNA regulation of expression of the cystic fibrosis transmembrane conductance regulator gene", Biochemical Journal, Jul. 27, 2011, pp. 25-32, vol. 12, No. 1.
Oglesby et al., "Regulation of Cystic Fibrosis Transmembrane Conductance Regulator by MicroRNA-145, -223, and -494 Is Altered in F508 Cystic Fibrosis Airway Epithelium", The Journal of Immunology, Feb. 22, 2013, pp. 3354-3362, vol. 190, No. 7.

* cited by examiner

*Primary Examiner* — Kimberly Chong
(74) *Attorney, Agent, or Firm* — Whitham, Curtis & Cook, P.C.

(57) ABSTRACT

The present invention relates to a method and compositions for the treatment of cystic fibrosis.

6 Claims, 15 Drawing Sheets

US 9,688,990 B2

METHODS AND PHARMACEUTICAL COMPOSITIONS FOR TREATMENT OF CYSTIC FIBROSIS

FIELD OF THE INVENTION

Figure 1:
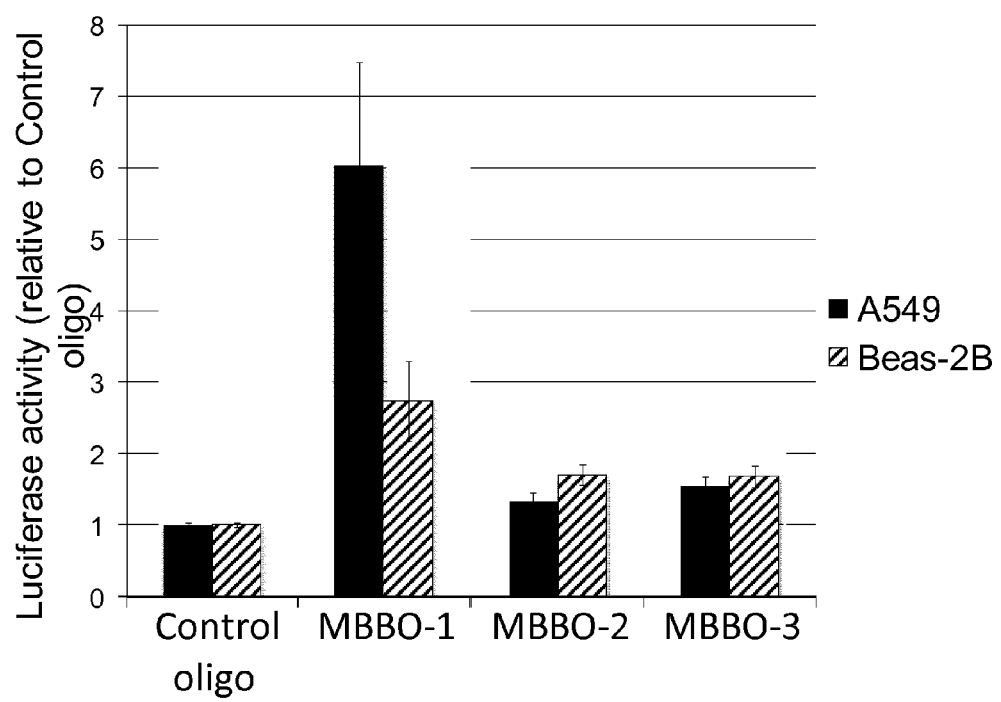
Figure 1:
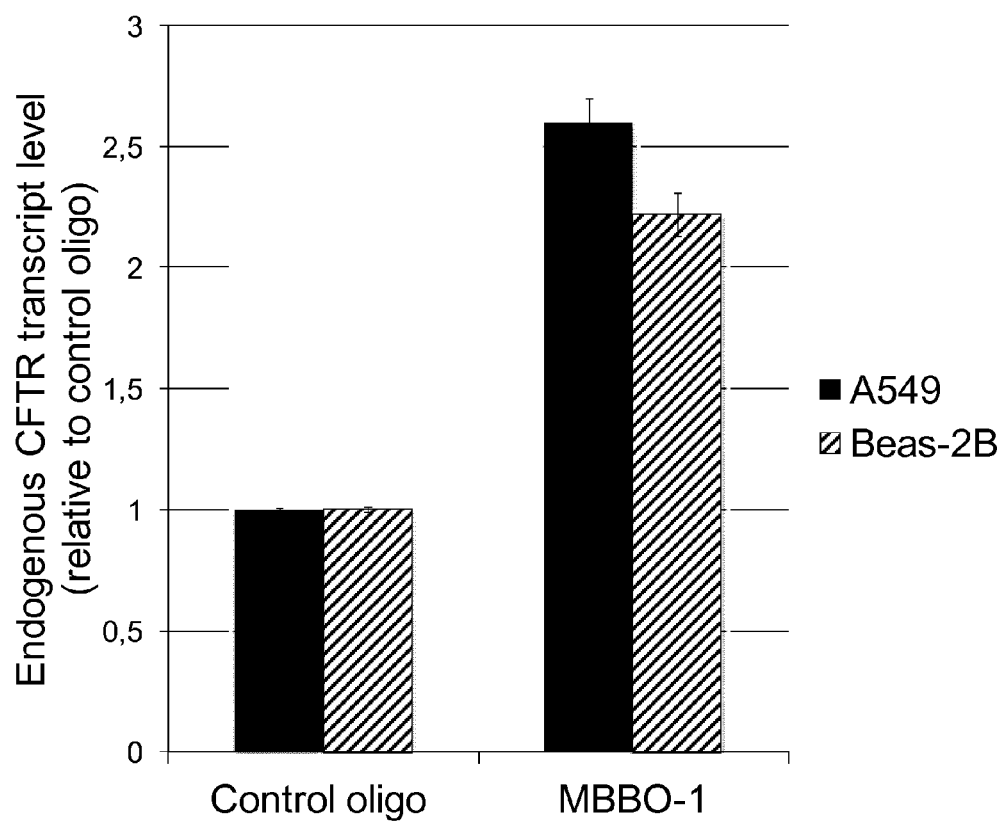
Figure 1:
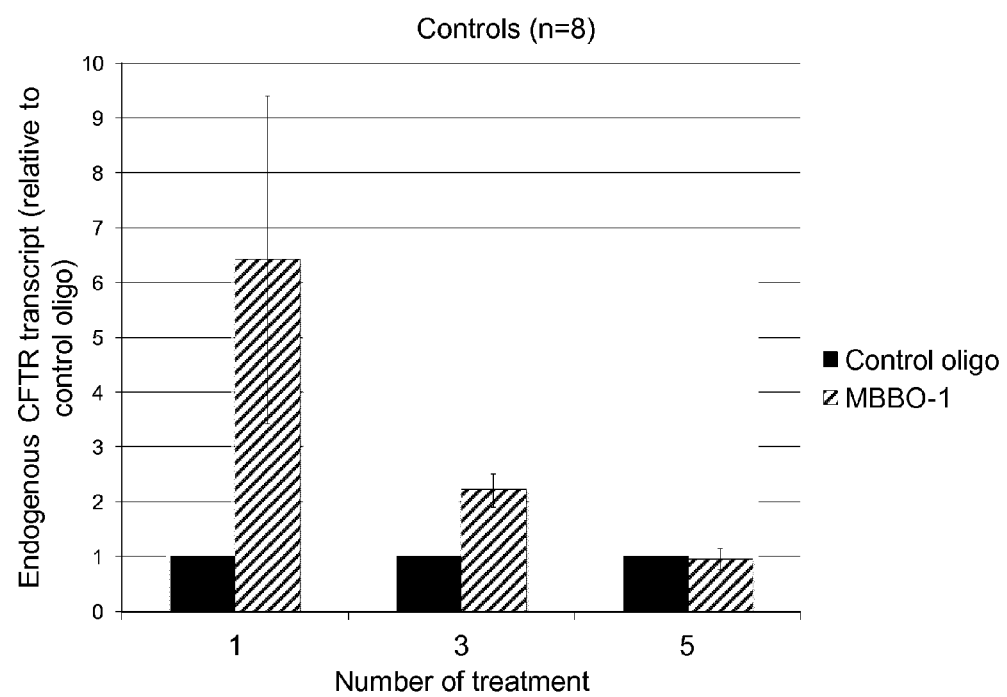
Figure 1:
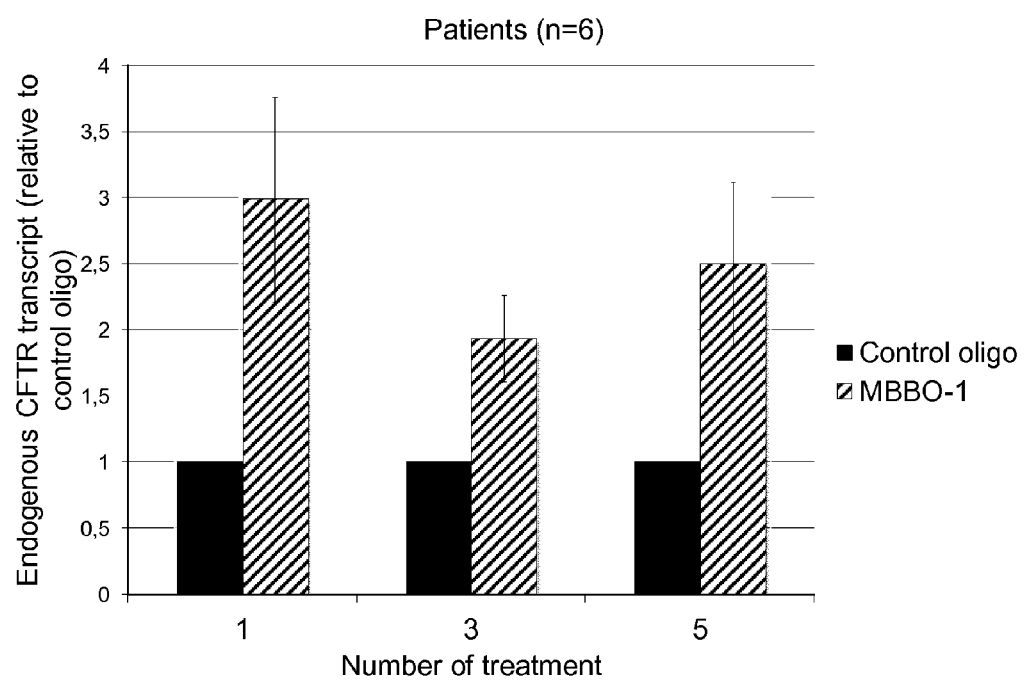
Figure 1:
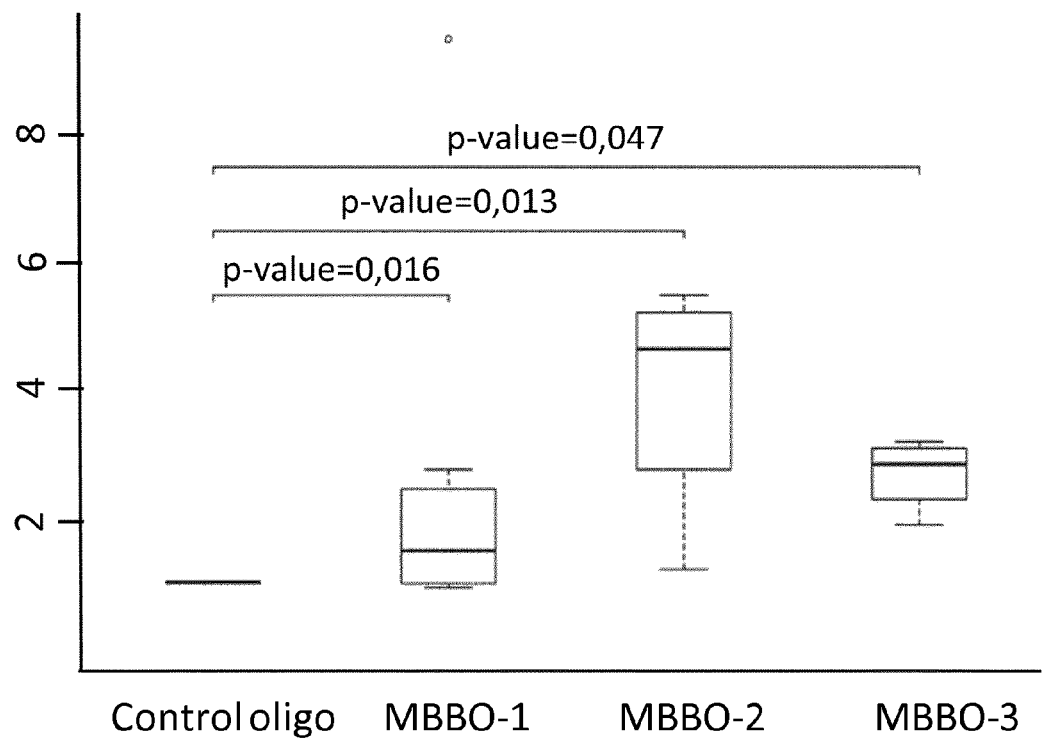
Figure 1:
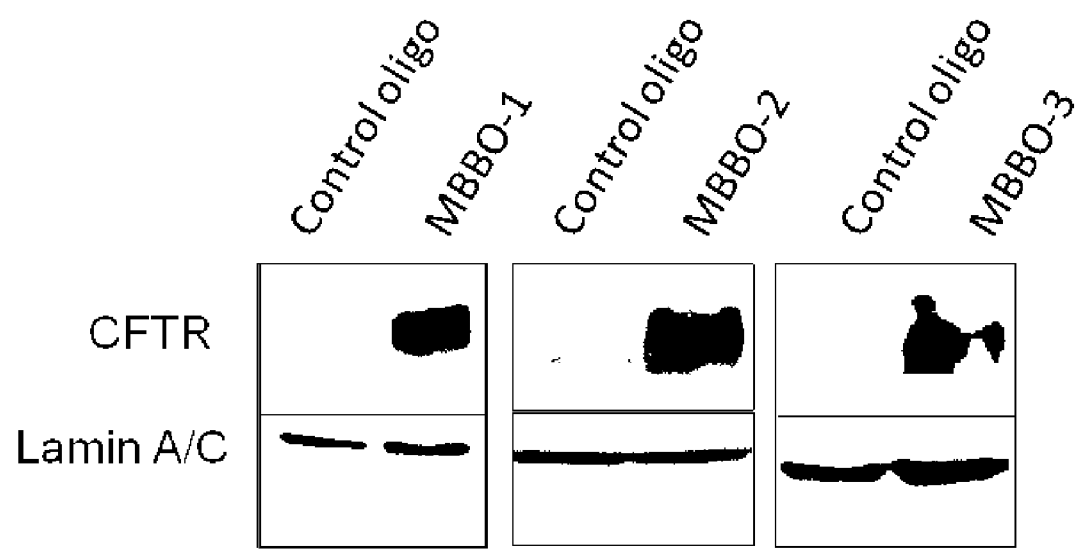
Figure 1:
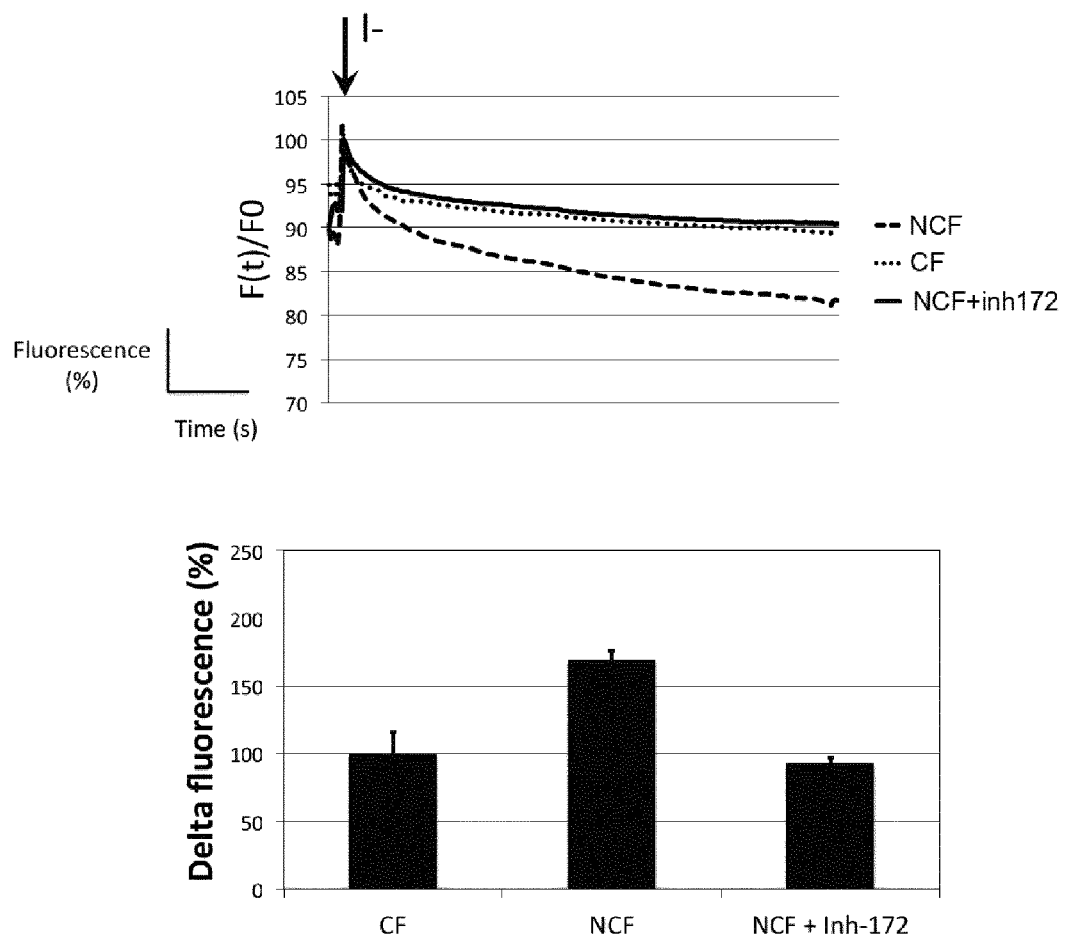
Figure 1:
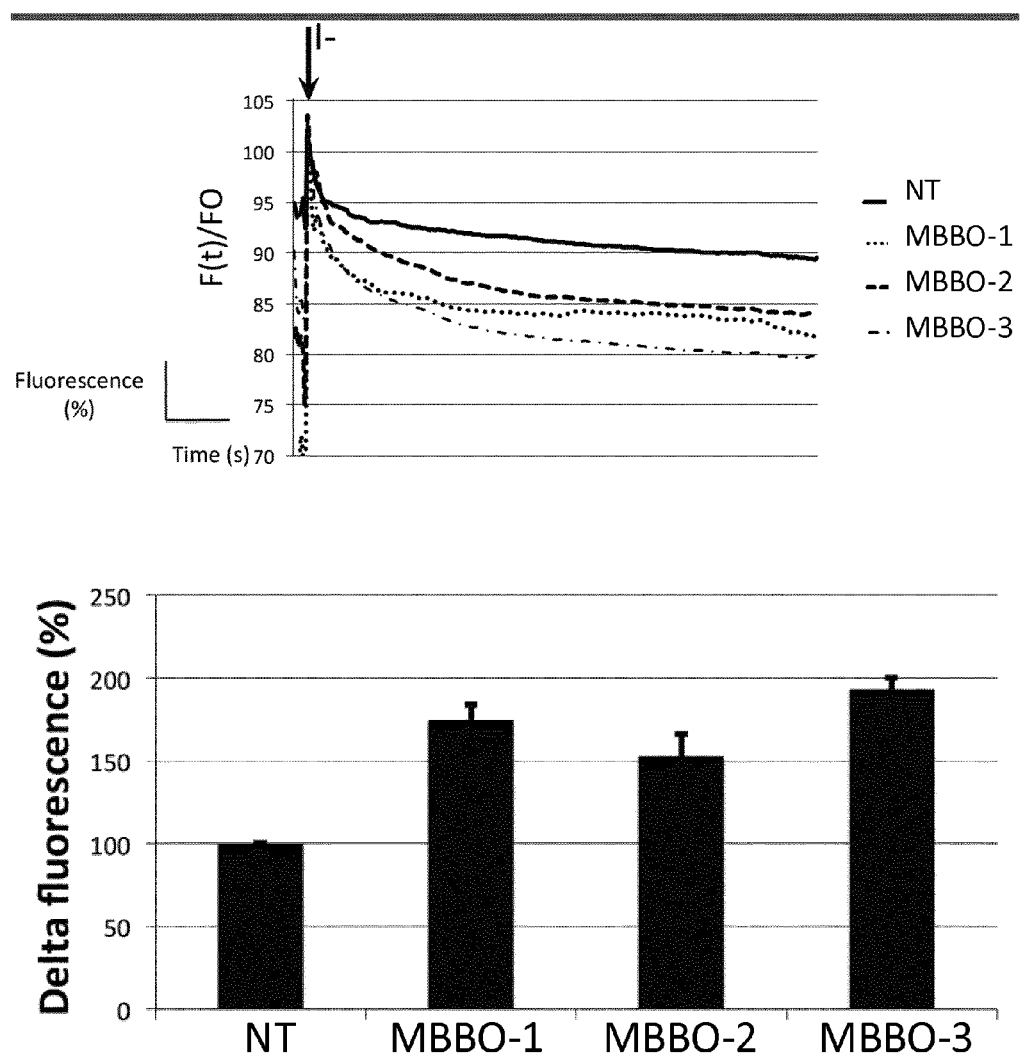

The present invention relates to a method and compositions for the treatment of cystic fibrosis.

BACKGROUND OF THE INVENTION

Cystic fibrosis (CF) is the most common lethal monogenic disorder in Caucasians, with an incidence of one bird in 2500-4000 and 70,000 affected people worldwide and kills most of them in their 20s. Cystic fibrosis is an autosomal recessive disease linked to mutations in the cystic fibrosis transmembrane conductance regulator gene (CFTR) gene whose nature determines the clinical expression and severity of the disease, affecting mainly the respiratory, digestive and genital systems. CFTR, a chloride-ion channel, is involved in the changes of surface liquid covering airway epithelial cells. Dehydration of the surface liquid leads to altered mucociliary clearance and inflammation and infections at the mucosal epithelia. CFTR mutations that reduce CFTR protein function cause accumulation of thick, sticky mucus in the bronchi of the lungs, loss of exocrine pancreatic function, impaired intestinal secretion, and an increase in the concentration of chloride in the sweat (Boucher R C Trends Mol Med., 2007). In patients with CF, lack of CFTR Cl(−) channel function leads to progressive pulmonary damage and ultimately to death. Chronic lung disease is the major cause of mortality and morbidity in CF patients.

Patients with CF require numerous therapies to manage these symptoms (Farrell P M et al. J Pediatr, 2008), including mucolytic and antibiotic agents and chest physiotherapy to treat the airway disease and digestive enzymes to replace the loss of exocrine pancreatic function. These and other interventions have increased life expectancy dramatically, but improvement is needed to reduce the high treatment burden and increase survival (Sawicki G S et al. J Cyst Fibros, 2009). A CFTR potentiator (Ivacaftor) has been developped by Vertex Pharmaceuticals (Ramsey B W et al. N Engl J Med, 2011) and has been recently approved for the treatment of CF patients carrying the p.Gly551Asp mutation (2-5% of all patients). To date, the drug has failed for CF patients with p.Phe508del, the most common mutations. Several CFTR correctors have been previously reported to be active in vitro (Hutt D M et al. Nature Chem Biol, 2010; Verkman A S and Galietta L J Nat Rev Drug Discov, 2009) but therapies for CF have not yet advanced from these efforts. A corrector that corrects the trafficking of the p.Phe508del protein is still under investigation in clinical trials (Van Goor F et al. PNAS, 2011).

Accordingly, there is a need to develop new drugs that will be suitable for preventing or treating CF and CFTR-related diseases. In this way, it has been suggested that characterization of new therapeutic compounds in CF and CFTR-related diseases may be highly desirable.

Since the cloning of the CFTR gene in 1989, nearly 2000 mutations of the gene have been described. The p.Phe508del mutation (deletion of phenylalanine at position 508 of the protein) is the most frequent (70% of mutated alleles in patients with CF). This severe mutation impairs the maturation of CFTR protein and the protein fails to reach cell membrane. Other grouped according to their effect on the CFTR protein include mutations that result in a shortened protein, in a reduced chloride conductance, in a defective CFTR stability at the cell surface or in reduced numbers of CFTR transcripts due to incorrect splicing (Rowe S M et al. N Engl J Med, 2005).

Alternative splicing is a regulated process during gene expression that results in a single gene coding for multiple proteins, constituting important post-transcriptional regulation of eukaryotic gene expression. In this process, particular exons of a gene may be included within, or excluded from, the final, processed mRNA. Abnormal variations in splicing are also implicated in disease; a large proportion of human genetic disorders result from splicing variants. Different CFTR mutations in splice sites or cis-acting splicing regulatory sites or resulting in the creation of new abnormal alternative donor or acceptor site may lead to mis-splicing of multiple abnormal CFTR transcripts and non functional CFTR proteins.

In addition to alternative splicing mechanisms, microRNAs (miRNA) can act in synchrony with transcription factors to control gene expression (Martinez N J et al. Bioessays, 2009; Shalgy R et al. Aging, 2009), revealing an important new complexity in the post-transcriptional regulation of eukaryotic gene expression. Recently, it has been found that CFTR is post-transcriptionally regulated by miRNAs, such as miR-145 and miR-494 (Gillen A E et al. Biochem J, 2011; Megiorni F et al. Plos One, 2011; Ramachandran S et al. PNAS, 2012). Several miRNAs including miR-145 are expressed in primary human airway epithelial cells, where CFTR expression is repressed (Gillen A E et al. Biochem J, 2011) or are deregulated in CF patients (Oglesby I K et al. J immunol, 2013; Ramachandran S et al. AJRCMB, 2013).

SUMMARY OF THE INVENTION

The present invention relates to methods and compositions for the treatment of CFTR-related disease and cystic fibrosis.

DETAILED DESCRIPTION OF THE INVENTION

In the present invention and in the objective to identify new repressive elements to design new tools for Cystic fibrosis (CF) correction, the inventors investigated the role of post-transcriptional regulation of CFTR gene expression in CF. Through the identification of a molecular network involving lung developmental-specific transcription factors and miRNAs controlling CFTR gene expression, the inventors established the importance of inhibitory motifs for the binding of regulators including miR-101, miR-145. By global profiling, the inventors also evidenced that miR-145 is one of the most deregulated microRNAs in adult versus fetal lung. Identifying cis- and trans-repressors allowed the inventors to envision new therapeutic tools for lung disease including cystic fibrosis (CF), and tested in reconstituted epithelia from nasal cells of p.Phe508del CF patients and in CF bronchial epithelial cells. After defining the regulatory motifs on the CFTR gene for the binding of the miRNAs of interest, the inventors then designed target-site blocker (TSB) (miRNA binding-blocker oligonculeotides (MBBO)) to prevent binding of several miRNAs including miR-101, miR-600, miR-145 and miR-384 to the 3'UTR of the CFTR gene.

The inventors have also investigated several mutations creating new abnormal alternative donor or acceptor site and then inducing alternative splicing resulting in abnormal CFTR transcripts and non functional CFTR proteins. The inventors then designed target-site blocker (TSB) targeting splice sites to prevent the binding of spliceosome proteins to the alternative donor and acceptor sites of the CFTR transcripts.

Therefore, by using these specific TSB oligonucleotides, the inventors demonstrate the correction of the CFTR channel activity through either an increase of the CFTR transcripts and protein levels or the restoration of the CFTR full-length transcripts.

Oligonucleotides of the Invention

The present invention relates to isolated, synthetic or recombinant oligonucleotides recognizing or targeting CFTR mRNA.

The term "oligonucleotide" refers to isolated, synthetic or recombinant oligonucleotides recognizing or targeting CFTR mRNA. The term "oligonucleotide" also refers to antisense oligonucletotide (ASO) or blocker oligonucleotide (BO) or target-site blocker (TSB) recognizing or targeting regulatory motifs on the CFTR mRNA. The term "oligonucleotides" also refers to miRNA binding-blocker oligonculeotides (MBBO) recognizing or targeting regulatory motifs on the CFTR mRNA to prevent binding of several miRNAs including miR-101, miR-600, miR-145 and miR-384 to the 3'UTR of the CFTR mRNA. The term "oligonucleotide" also refers to splicing-blocker oligonucleotides (SBO) recognizing or targeting splice sites to prevent the binding of spliceosome proteins to the alternative donor and acceptor sites of the CFTR mRNA and the splicing of a cryptic exon inserted into the mutant CFTR mRNA.

The term "CFTR" refers to cystic fibrosis transmembrane conductance regulator, an ATP-binding cassette (ABC) transporter-class ion channel involved in the transport of chloride and thiocyanate ions across epithelial cell membranes. The term "CFTR" also refers to a chloride-ion channel involved in the changes of surface liquid covering airway epithelial cells.

The present invention also relates to an isolated, synthetic or recombinant oligonucleotide comprising a nucleic acid sequence that has at least about 90%, or at least about 95%, or at least about 96%, or at least about 97%, or at least about 98%, or at least about 99% nucleic acid sequence identity with a sequence selected from the group consisting of SEQ ID NO: 1, SEQ ID NO: 2, SEQ ID NO: 3, SEQ ID NO: 4 and SEQ ID NO: 5.

Nucleic acid sequence identity is preferably determined using a suitable sequence alignment algorithm and default parameters, such as BLAST N (Karlin and Altschul, Proc. Natl Acad. Sci. USA 87(6):2264-2268 (1990)).

In a particular embodiment, the oligonucleotide according to the invention comprises a nucleic acid sequence selected from the group consisting of SEQ ID NO: 1, SEQ ID NO: 2, SEQ ID NO: 3, SEQ ID NO: 4 and SEQ ID NO: 5.

In a particular embodiment, the oligonucleotide according to the invention has a nucleic acid sequence selected from the group consisting of SEQ ID NO: 1, SEQ ID NO: 2, SEQ ID NO: 3, SEQ ID NO: 4 and SEQ ID NO: 5.

The oligonucleotide of the invention may be of any suitable type. The one skilled in the art can easily provide some modifications that will improve the clinical efficacy of the oligonucleotide (C. Frank Bennett and Eric E. Swayze, RNA Targeting Therapeutics: Molecular Mechanisms of Antisense Oligonucleotides as a Therapeutic PlatformAnnu Rev. Pharmacol. Toxicol. 2010.50:259-293.). Typically, chemical modifications include backbone modifications, heterocycle modifications, sugar modifications, and conjugations strategies. For example the oligonucleotide may be selected from the group consisting of oligodeoxyribonucleotides, oligoribonucleotides, LNA, oligonucleotide, morpholinos, tricyclo-DNA-antisense oligonucleotides (ASOs), U7- or U1-mediated ASOs or conjugate products thereof such as peptide-conjugated or nanoparticle-complexed ASOs. Indeed, for use in vivo, the oligonucleotide may be stabilized. A "stabilized" oligonucleotide refers to an oligonucleotide that is relatively resistant to in vivo degradation (e.g. via an exo- or endo-nuclease). Stabilization can be a function of length or secondary structure. In particular, oligonucleotide stabilization can be accomplished via phosphate backbone modifications.

In a particular embodiment, the oligonucleotide according to the invention is a LNA oligonucleotide. As used herein, the term "LNA" (Locked Nucleic Acid) (or "LNA oligonucleotide") refers to an oligonucleotide containing one or more bicyclic, tricyclic or polycyclic nucleoside analogues also referred to as LNA nucleotides and LNA analogue nucleotides. LNA oligonucleotides, LNA nucleotides and LNA analogue nucleotides are generally described in International Publication No. WO 99/14226 and subsequent applications; International Publication Nos. WO 00/56746, WO 00/56748, WO 00/66604, WO 01/25248, WO 02/28875, WO 02/094250, WO 03/006475; U.S. Pat. Nos. 6,043,060, 6,268,490, 6,770,748, 6,639,051, and U.S. Publication Nos. 2002/0125241, 2003/0105309, 2003/0125241, 2002/0147332, 2004/0244840 and 2005/0203042, all of which are incorporated herein by reference. LNA oligonucleotides and LNA analogue oligonucleotides are commercially available from, for example, Proligo LLC, 6200 Lookout Road, Boulder, Colo. 80301 USA.

Other possible stabilizing modifications include phosphodiester modifications, combinations of phosphodiester and phosphorothioate modifications, methylphosphonate, methylphosphorothioate, phosphorodithioate, p-ethoxy, and combinations thereof. Chemically stabilized, modified versions of the oligonucleotide also include "Morpholinos" (phosphorodiamidate morpholino oligomers, PMOs), 2'-O-Met oligomers, tricyclo (tc)-DNAs, U7 short nuclear (sn) RNAs, or tricyclo-DNA-oligoantisense molecules (U.S. Provisional Patent Application Ser. No. 61/212,384 For: Tricyclo-DNA Antisense Oligonucleotides, Compositions and Methods for the Treatment of Disease, filed Apr. 10, 2009, the complete contents of which is hereby incorporated by reference).

Other forms of oligonucleotides of the present invention are oligonucleotide sequences coupled to small nuclear RNA molecules such as U1 or U7 in combination with a viral transfer method based on, but not limited to, lentivirus or adeno-associated virus (Denti, M A, et al, 2008; Goyenvalle, A, et al, 2004).

The oligonucleotide of the invention can be synthesized de novo using any of a number of procedures well known in the art. For example, the b-cyanoethyl phosphoramidite method (Beaucage et al., 1981); nucleoside H-phosphonate method (Garegg et al., 1986; Froehler et al., 1986, Garegg et al., 1986, Gaffney et al., 1988). These chemistries can be performed by a variety of automated nucleic acid synthesizers available in the market. These nucleic acids may be referred to as synthetic nucleic acids. Alternatively, oligonucleotide can be produced on a large scale in plasmids (see Sambrook, et al., 1989). Oligonucleotide can be prepared from existing nucleic acid sequences using known techniques, such as those employing restriction enzymes, exonucleases or endonucleases. Oligonucleotide prepared in this manner may be referred to as isolated nucleic acids.

In a particular embodiment, the oligonucleotide of the present invention is conjugated to a second molecule. Typically said second molecule is selected from the group consisting of aptamers, antibodies or polypeptides. For example, the oligonucleotide of the present invention may be conjugated to a cell penetrating peptide. Cell penetrating peptides are well known in the art and include for example the TAT peptide (Bechara C, Sagan S. Cell-penetrating peptides: 20 years later, where do we stand? FEBS Lett. 2013 Jun. 19; 587(12):1693-702). In a particular embodiment, the second molecule is able to target the epithelial cell. In a particular embodiment, the molecule targets the CFTR transporter. Several antibodies, peptides and aptamers that bind with high affinity to epithelial cell are described in Raksha J et al. Am J Respir Cell Mol Biol. 2010; Van Meegen M A et al. Plos One. 2011).

Therapeutic Methods and Uses of the Invention

The oligonucleotide of the invention may be used in a method of preventing or treating diseases in a subject in need thereof.

Therefore, a further aspect of the invention relates to the oligonucleotide of the invention for use as a medicament.

In one embodiment, the oligonucleotide according to the invention may be used in the prevention or treatment of CFTR-related disease in a subject in need thereof.

The present invention also relates to the oligonucleotide according to the invention for use in the prevention or treatment of cystic fibrosis in a subject in need thereof.

As used herein, the term "subject" denotes a mammal. In one embodiment of the invention, a subject according to the invention refers to any subject (preferably human) afflicted or at risk to be afflicted with CFTR-related diseases. In a preferred embodiment of the invention, a subject according to the invention refers to any subject (preferably human) afflicted or at risk to be afflicted with cystic fibrosis.

The method of the invention may be performed for any type of CFTR-related disease such as pulmonary diseases, chronic obstructive pulmonary disease (COPD), lung cancer, Congenital absence of the vas deferens (CAVD), Idiopathic chronic pancreatitis (ICP), bronchiectasis. In the context of the invention, CFTR-related disease can be diagnosed in a subject and determined in a biological sample with techniques that are well known from the one skilled in the art. These methods include, without being limited, amplification methods such as quantitative PCR, CFTR gene sequencing, and splicing reporter assays.

The method of the invention may also be performed for any type of cystic fibrosis such as revised in the World Health Organisation Classification of cystic fibrosis and selected from the E84 group: mucoviscidosis, Cystic fibrosis with pulmonary manifestations, Cystic fibrosis with intestinal manifestations and Cystic fibrosis with other manifestations.

In a particular embodiment, oligonucleotides of the invention may be delivered in vivo alone or in association with a vector. In its broadest sense, a "vector" is any vehicle capable of facilitating the transfer of the oligonucleotide of the invention to the cells. Preferably, the vector transports the nucleic acid to cells with reduced degradation relative to the extent of degradation that would result in the absence of the vector. In general, the vectors useful in the invention include, but are not limited to, naked plasmids, non viral delivery systems (cationic transfection agents, liposomes, etc. . . . ), phagemids, viruses, other vehicles derived from viral or bacterial sources that have been manipulated by the insertion or incorporation of the oligonucleotide sequences. Viral vectors are a preferred type of vector and include, but are not limited to nucleic acid sequences from the following viruses: RNA viruses such as a retrovirus (as for example moloney murine leukemia virus and lentiviral derived vectors), harvey murine sarcoma virus, murine mammary tumor virus, and rous sarcoma virus; adenovirus, adeno-associated virus; SV40-type viruses; polyoma viruses; Epstein-Barr viruses; papilloma viruses; herpes virus; vaccinia virus; polio virus. One can readily employ other vectors not named but known to the art. In a preferred embodiment, the oligonucleotide sequence is under the control of a heterologous regulatory region, e.g., a heterologous promoter. The promoter can also be, e.g., a viral promoter, such as CMV promoter or any synthetic promoters.

In a particular embodiment, two or even more oligonucleotides can also be used at the same time; this may be particularly interesting when the oligonucleotides are vectorized within an expression cassette (as for example by U7 or U1 cassettes).

The present invention also relates to the oligonucleotide according to the invention in combination with one or more anti-CFTR-related disease agent for use in the prevention or treatment of CFTR-related disease in a subject in need thereof.

The present invention also relates to the oligonucleotide according to the invention in combination with one or more anti-cystic fibrosis agent for use in the prevention or treatment of cystic fibrosis in a subject in need thereof.

In one embodiment, the anti-cystic fibrosis agent or anti-CFTR-related disease agent may include a CFTR corrector or potentitator (such as ivacaftor (VX-770, Kalydeco), VX-661, VX-809), osmotic agents (such as Bronchitol), antioxidants drugs, modifier of mucus (such as Pulmozyme, Mucomyst), bronchodilatators (such as Ventolin, Serevent), anti-infective compounds (such as TOBI, Azithromycin, Josacine) or further anti-inflammatory drugs (such as Ibuprofen, Dexamethasone, Zyflo, Accolate).

The present invention also relates to a method for preventing or treating CFTR-related disease in a subject in need thereof, comprising the step of administering to said subject the oligonucleotide according to the invention.

The present invention also relates to a method for preventing or treating cystic fibrosis in a subject in need thereof, comprising the step of administering to said subject the oligonucleotide of the invention.

The present invention also relates to a method for preventing or treating CFTR-related disease in a subject in need thereof, comprising the step of administering to said subject the oligonucleotide according to the invention in combination with one or more anti-CFTR-related disease agent.

The present invention also relates to a method for preventing or treating cystic fibrosis in a subject in need thereof, comprising the step of administering to said subject the oligonucleotide according to the invention in combination with one or more anti-cystic fibrosis agent.

Pharmaceutical Compositions and Kits of the Invention

The oligonucleotide of the invention may be used or prepared in a pharmaceutical composition.

In one embodiment, the invention relates to a pharmaceutical composition comprising the oligonucleotide of the invention and a pharmaceutical acceptable carrier for use in the prevention or treatment of CFTR-related disease in a subject in need thereof.

The present invention also relates to a pharmaceutical composition comprising the oligonucleotide of the invention and a pharmaceutical acceptable carrier for use in the prevention or treatment of cystic fibrosis in a subject in need thereof.

Typically, the compound of the invention may be combined with pharmaceutically acceptable excipients, and optionally sustained-release matrices, such as biodegradable polymers, to form therapeutic compositions.

"Pharmaceutically" or "pharmaceutically acceptable" refer to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

In the pharmaceutical compositions of the present invention for oral, inhalation, sublingual, subcutaneous, intramuscular, intravenous, transdermal, local or rectal administration of the oligonucleotide, alone or in combination with another active principle, can be administered in a unit administration form, as a mixture with conventional pharmaceutical supports, to animals and human beings. Suitable unit administration forms comprise oral-route forms such as tablets, gel capsules, powders, granules and oral suspensions or solutions, sublingual and buccal administration forms, inhalation administration forms, aerosols, implants, subcutaneous, transdermal, topical, intraperitoneal, intramuscular, intravenous, subdermal, transdermal, intrathecal and nasal or intranasal administration forms and rectal administration forms.

Preferably, the pharmaceutical compositions contain vehicles which are pharmaceutically acceptable for a formulation capable of being administered by nasal administration or by inhalation. Nasal administration may be under the form of liquid solution, suspension or emulsion. Solutions and suspensions are administered as drops. Solutions can also be administered as a fine mist from a nasal spray bottle or from a nasal inhaler Inhalation may be accomplished under the form of solutions, suspensions, and powders; these formulations are administered via an aerosol, droplets or a dry powder inhaler. The powders may be administered with insufflators or puffers.

Pharmaceutical compositions of the present invention include a pharmaceutically or physiologically acceptable carrier such as saline, sodium phosphate, etc. The compositions will generally be in the form of a liquid, although this need not always be the case. Suitable carriers, excipients and diluents include lactose, dextrose, sucrose, sorbitol, mannitol, starches, gum acacia, calcium phosphates, alginate, tragacanth, gelatin, calcium silicate, microcrystalline cellulose, polyvinylpyrrolidone, celluose, water syrup, methyl cellulose, methyl and propylhydroxybenzoates, mineral oil, etc. The formulations can also include lubricating agents, wetting agents, emulsifying agents, preservatives, buffering agents, etc. Those of skill in the art will also recognize that nucleic acids are often delivered in conjunction with lipids (e.g. cationic lipids or neutral lipids, or mixtures of these), frequently in the form of liposomes or other suitable micro- or nano-structured material (e.g. micelles, lipocomplexes, dendrimers, emulsions, cubic phases, etc.).

One skilled in the art will recognize that the amount of an oligonucleotide to be administered will be an amount that is sufficient to induce amelioration of unwanted disease symptoms. Such an amount may vary inter alia depending on such factors as the gender, age, weight, overall physical condition, of the subject, etc. and may be determined on a case by case basis. The amount may also vary according to the type of condition being treated, and the other components of a treatment protocol (e.g. administration of other medicaments such as steroids, etc.). If a viral-based delivery of oligonucleotides is chosen, suitable doses will depend on different factors such as the viral strain that is employed, the route of delivery (intramuscular, intravenous, intra-arterial, oral, inhalation or other). Those of skill in the art will recognize that such parameters are normally worked out during clinical trials. In addition, treatment of the subject is usually not a single event. Rather, the oligonucleotides of the invention will likely be administered on multiple occasions, that may be, depending on the results obtained, several days apart, several weeks apart, or several months apart, or even several years apart.

Pharmaceutical compositions of the invention may include any further agent which is used in the prevention or treatment of cystic fibrosis or CFTR-related disease. For example, pharmaceutical compositions of the invention can be co-administered with CFTR corrector or potentitator (such as ivacaftor VX-770, VX-661, VX-809, Kalydeco), osmotic agents (such as Bronchitol), antioxidants drugs, modifier of mucus (such as Pulmozyme, Mucomyst), bronchodilatators (such as Ventolin, Serevent), anti-infective compounds (such as TOBI, Azithromycin, Josacine) or further anti-inflammatory drugs (such as Ibuprofen, Dexamethasone, Zyflo, Accolate).

The invention also provides kits comprising at least one oligonucleotide of the invention. Kits containing oligonucleotide of the invention find use in therapeutic methods.

Oligonucleotide Sequences

```
SEQ ID NO: 1 for MBBO-1:
AGT GAT ATT TTC TTA CAG TAA T

SEQ ID NO: 2 for MBBO-2:
ATA AAC CGC TGA AGT TTC CAG TTA TC

SEQ ID NO: 3 for MBBO-3:
ACA TTA TTA AAA TAA ATA TTT CCT AGA G

SEQ ID NO: 4 for TSB1:
GTT GGT ACT TCT GTA ATA

SEQ ID NO: 5 for TSB2:
ACC TTA CTT ATA TCT CAA
```

The invention will be further illustrated by the following figures and examples. However, these examples and figures should not be interpreted in any way as limiting the scope of the present invention.

FIGURES

FIG. 1: Impact of miRNA-binding blocker oligonucleotides on CFTR expression in pulmonary cells.

(A) Impact of different MBBOs on the post-transcriptional regulation of the CFTR gene. MBBOs (100 nM) were transfected in A549 and Beas-2B pulmonary cells. Luciferase activity data are normalized to miRCURY LNA™ microRNA Inhibitor Negative Control A (control oligo). (B) Impact of MBBO-1 on the endogenous CFTR transcript level in A549 and Beas-2B pulmonary cells. CFTR mRNA level was assessed by RT-qPCR following the transfection of MBBO-1 or the use of the control oligo. Data are normalized to β-actin transcript level. (C) Impact of MBBO-1 on the endogenous CFTR transcript level in controls (n=8), or (D) in ALI epithelium cultured from p.Phe508del homozygous CF patients (n=6). CFTR mRNA level was assessed by RT-qPCR 24 h following 1, 3 or 5 treatments with MBBO-1 or the use of the control oligo. Data are normalized to β-actin transcript level. (E) Impact of MBBO-1, MBBO-2 and MBBO-3 on endogenous CFTR transcript level in CF patients. Box plot was assessed on CFTR transcript level in p.Phe508del homozygous CF patients (24 h after the first treatment with MBBO-1, MBBO-2, MBBO-3 or control oligo). Data are normalized to β-actin transcript level. (F) Impact of MBBO-1, MBBO-2 and MBBO-3 on endogenous CFTR protein level in CF patients. Immunoblots were performed with CFTR antibody (clone MM13-4) on total protein extract of p.Phe508del homozygous CF patients (24 h after the first treatment with MBBO-1, MBBO-2, MBBO-3 or control oligo). Data are normalized to Lamin A/C protein level. In reconstituted airway epithelium 100 nM of MBBOs were directly added to the apical side in free medium (without transfection reagent) for 2 hours in 37° C. CFTR activity (G) in 16HBEo-(NCF) and CFBE (CF) cells and (H) in non-treated (NT) CFBE cells or MBBO-treated CFBE cells. Representative cell fluorescence recordings from bronchial cells transiently expressing the halide-sensitive YFP (scale bar reports the percentage of total cell fluorescence). Extracellular addition of I⁻ (arrow) caused YFP quenching with a rate proportional to the rate of I⁻ influx and CFTR activity. Channel opening is detected by a decrease of the probe fluorescence. The amount of quench is directly proportional to the Cl⁻ efflux. Graph represents the summary of data obtained from the functional assay reporting rates of I transport.

Values are extremely significant at *P<0.0001.

Figure 2:
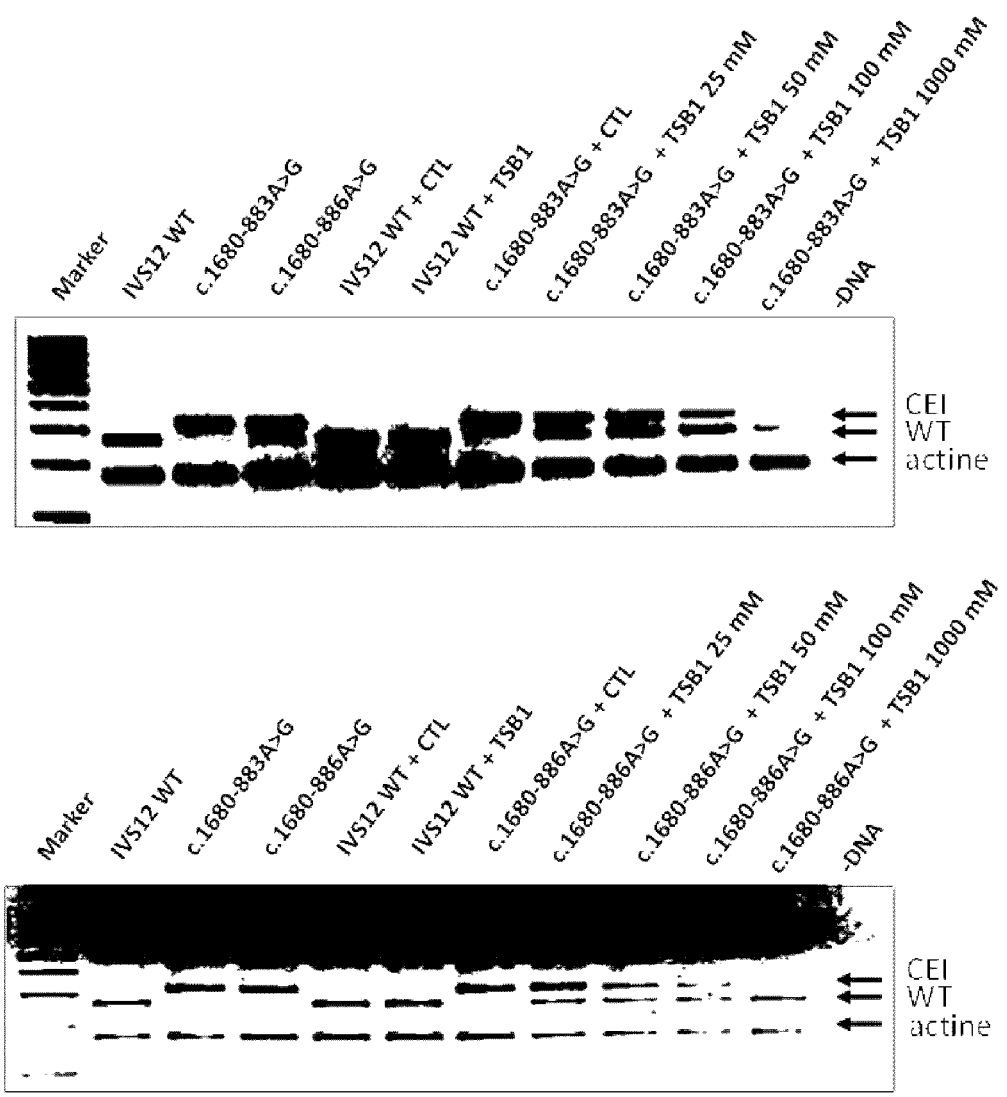
Figure 2:
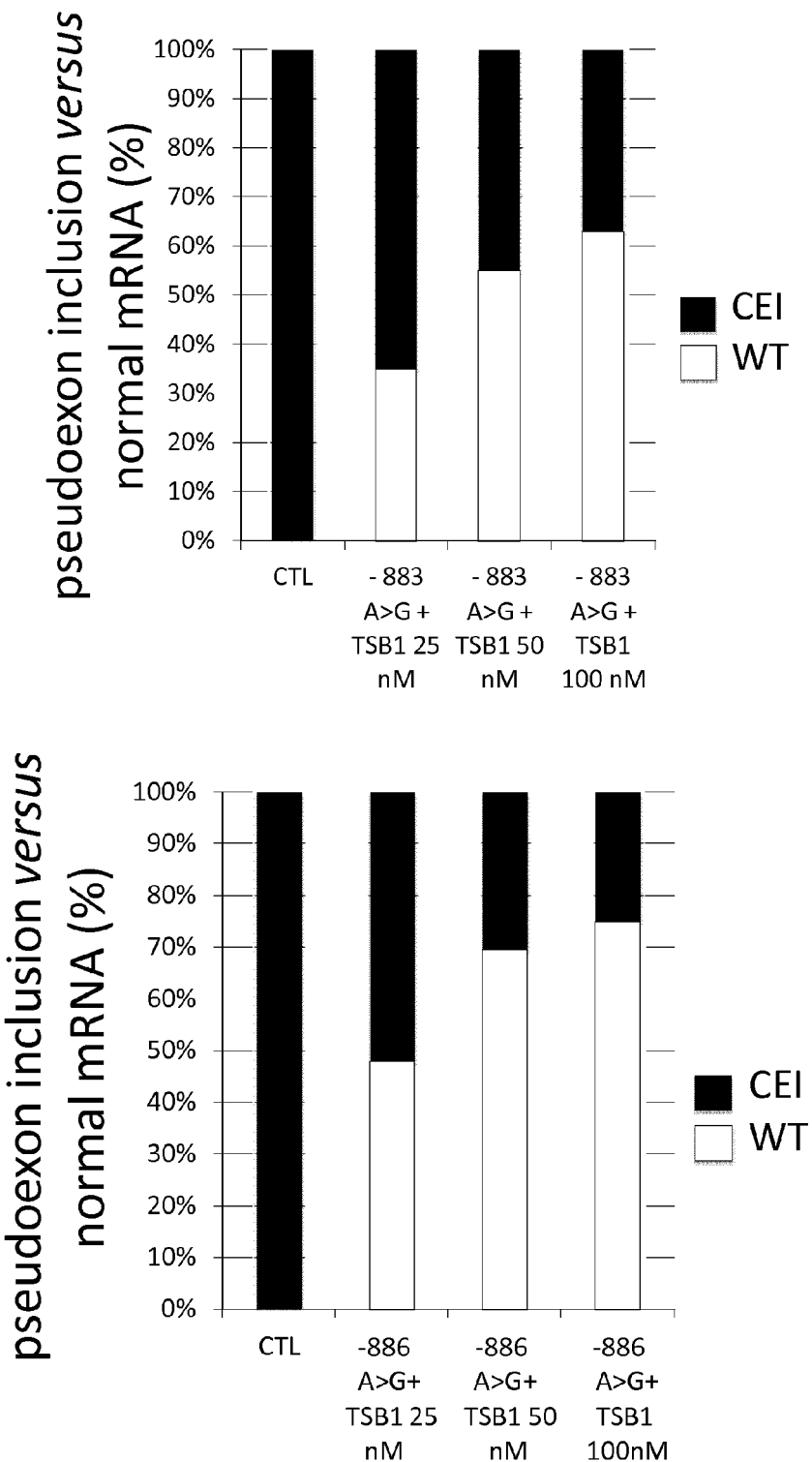
Figure 2:
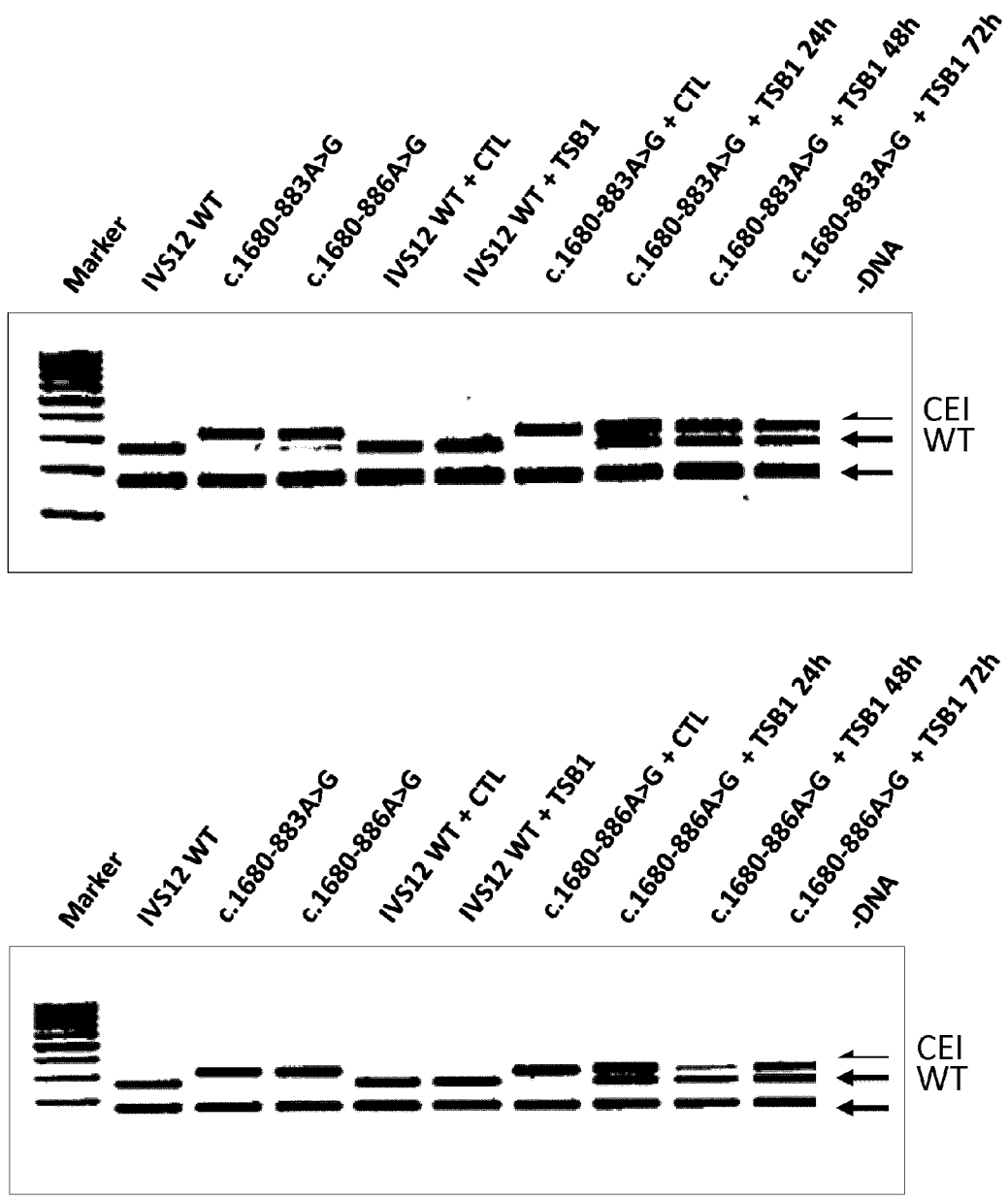
Figure 2:
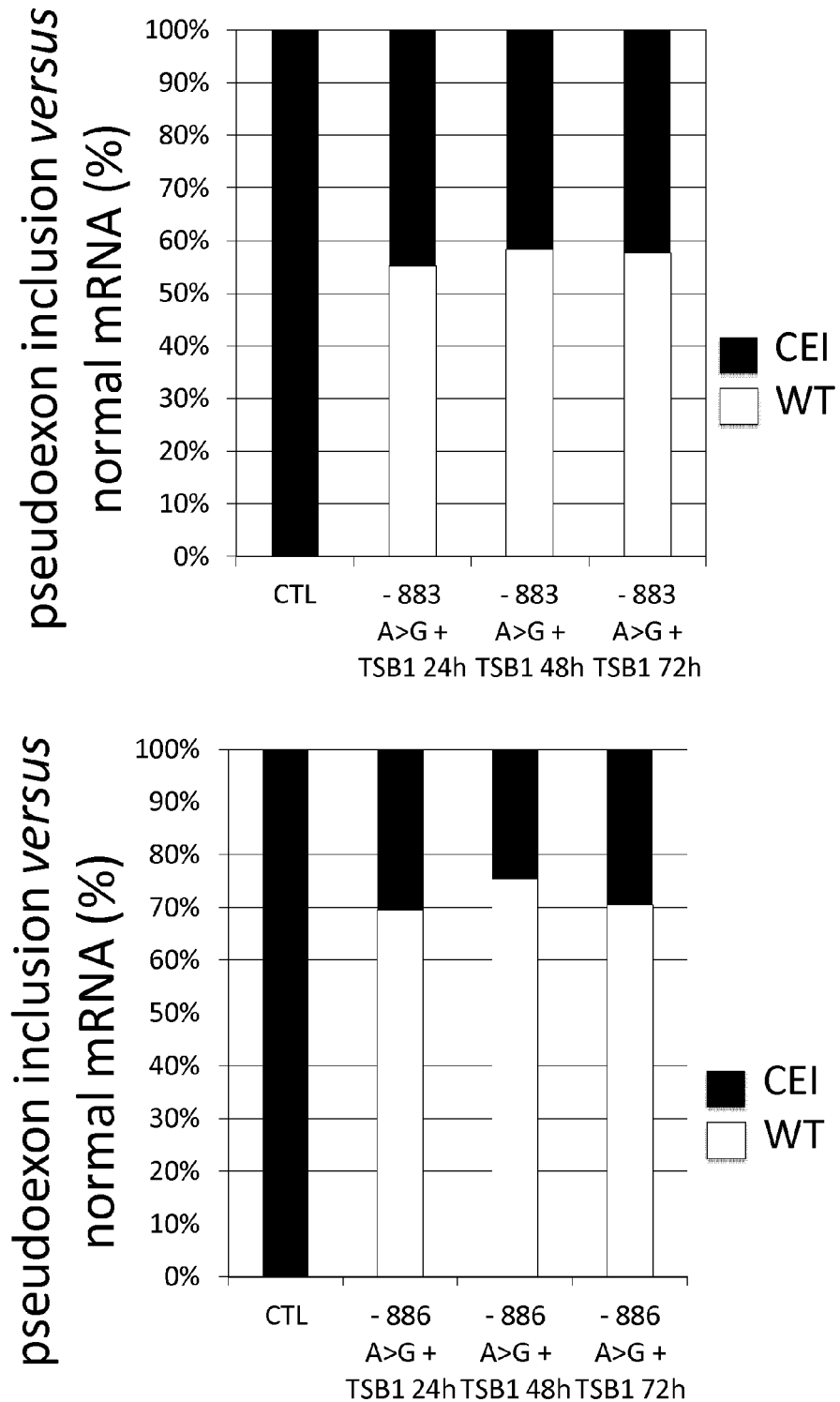
Figure 2:
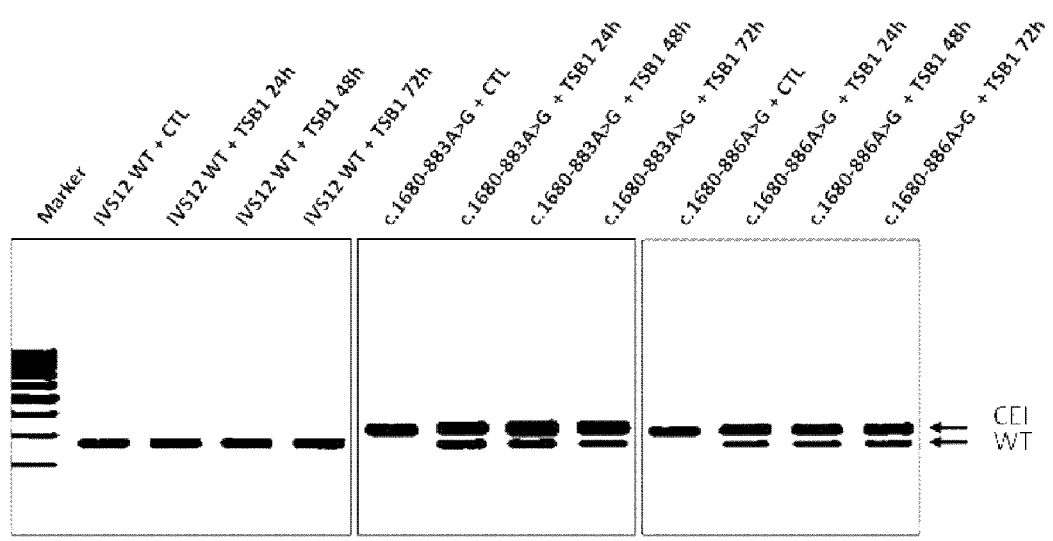
Figure 2:
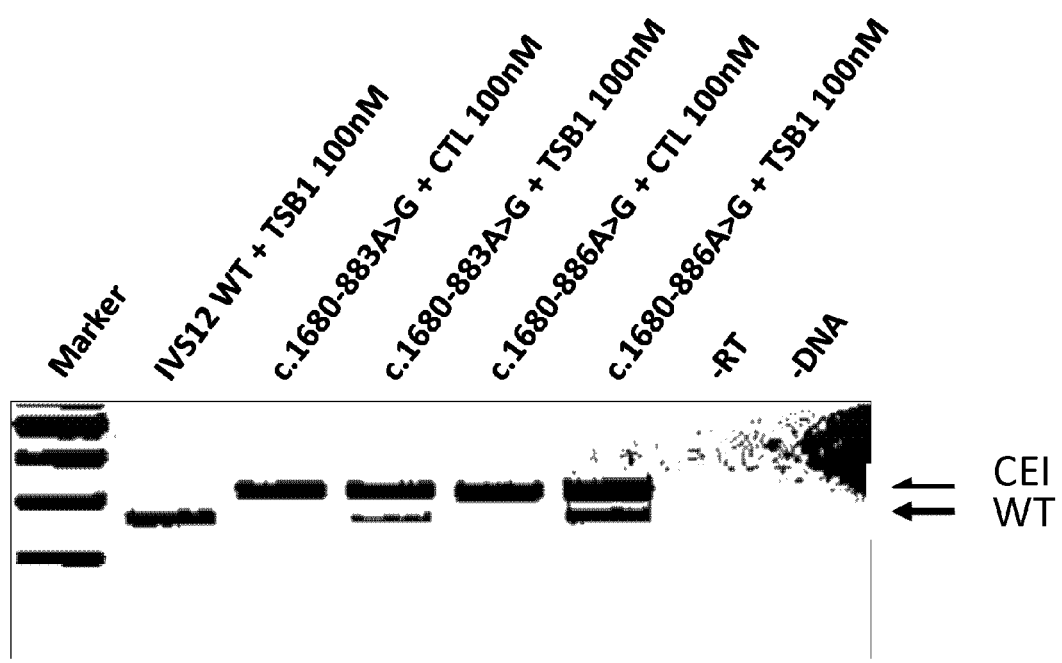

FIG. 2: Correction of aberrant splicing in bronchial cells by TSB1.

A and C. RT-PCR analysis of total RNA from bronchial BEAS-2B cells was performed using specific primers to analyse splicing after co-transfection of wild type (IVS12 wt) or mutant (c.1680-883A>G, c.1680-886A>G) minigenes and TSBs (WT, wildtype transcript and CEI, cryptic exon inclusion). A. Effect of TSB concentration on aberrant splicing. Cells were transfected with different TSB1 concentrations (25, 50, 100, 1000 nM) for 24 hours. C. Effect of incubation time (24 h, 48 h and 72 h) on splicing correction using 50 nM TSB1. TSB1 specificity was confirmed using a control TSB (CTL) at the different tested concentrations and in combination with wild type and mutant minigenes; to avoid overloading the figure, only the assays at 50 nM or 24 h were shown. B and D. Quantification of CEI and WT transcripts after transfection of TSBs at different concentrations (B) or at different time-points after transfection (D). RT-PCR was performed using a Fluorescein amidite (FAM)-labelled forward primer located within the splice donor exon and a reverse primer within the splice acceptor exon of the pSPL3 plasmid. The quantification, in percentage, was performed by dividing the area of the CEI peak by the area of all peaks (wild-type+CEI). Data correspond to the mean value of at least two independent experiments. E. RT-PCR analysis of total RNA was performed using specific primers to analyse both transcripts (WT, wild-type and CEI, cryptic exon inclusion). F. TSB1 was transfected 24 h at 100 nM in combination with WT or mutant minigenes in nasal cells obtained from a control individu, cultured one week in BEGM (Lonza, Walkersville, Md. USA) and plated in 24-well plates. RT-PCR analysis of total RNA was performed from nasal cells using specific primers to analyse both transcripts (WT, wild-type and CEI, cryptic exon inclusion).

Figure 3:
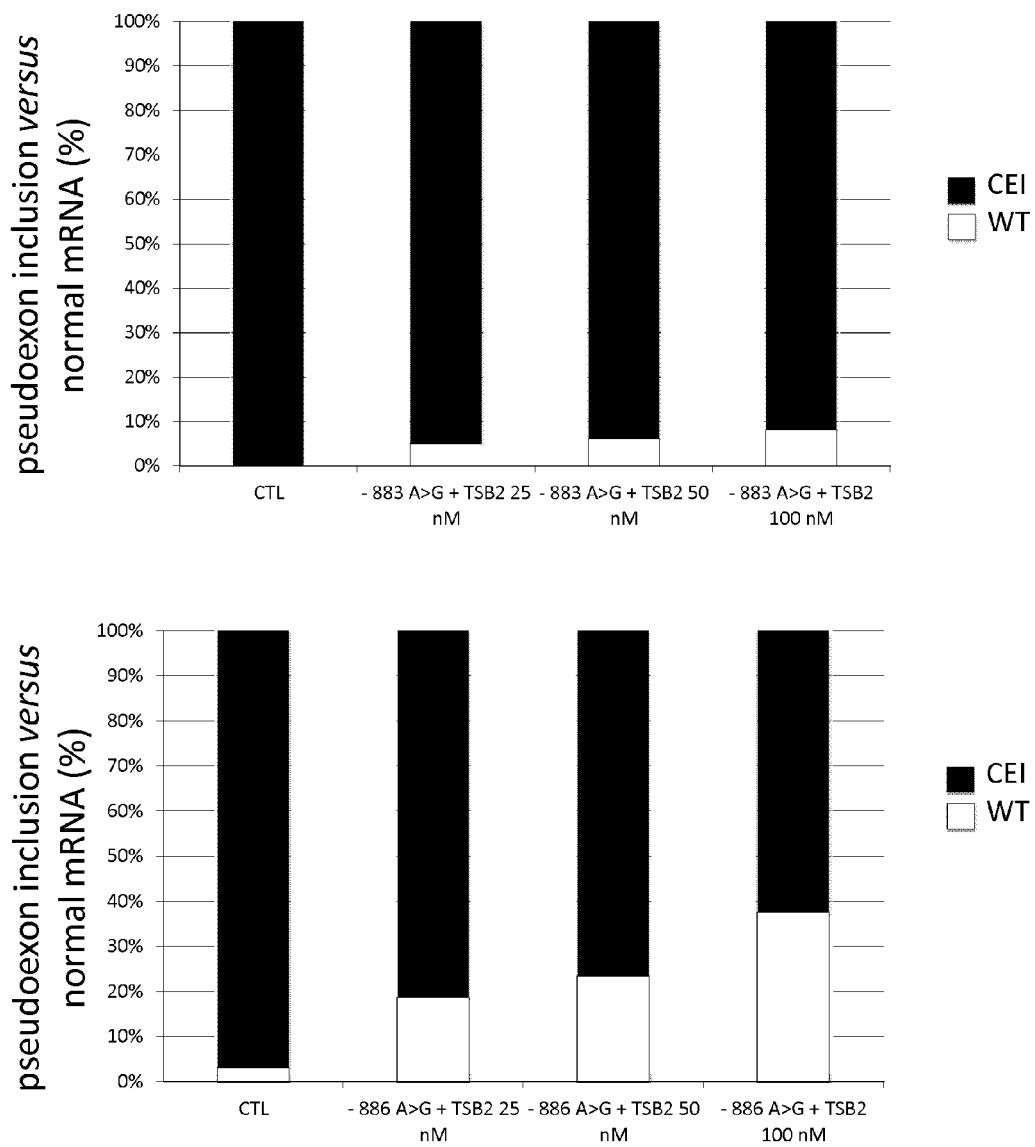

FIG. 3: Correction of aberrant splicing in bronchial cells by TSB2

Quantification of CEI and WT transcripts after co-transfection of TSB2 at different concentrations and the c.1680-883A>G or c.1680-886A>G minigenes. RT-PCR was performed using a Fluorescein amidite (FAM)-labelled forward primer located within the splice donor exon and a reverse primer within the splice acceptor exon of the pSPL3 plasmid. The quantification, in percentage, was performed by dividing the area of the CEI peak by the area of all peaks (wild-type+CEI). Data correspond to the mean value of at least two independent experiments. TSB2 specificity was confirmed by using a control TSB (CTL) at the different tested concentrations and in combination with both WT and mutant minigenes;

to avoid overloading the figure, only the assay at 50 nM is shown.

EXAMPLES

Example 1

Material & Methods

Gene Reporter Vectors and Directed Mutagenesis

The 3'UTR of the CFTR gene (1.7 kb from the termination codon to the poly-adenylation signal) was subcloned into the pGL3-Control vector (Promega) downstream of the Luciferase gene (pGL3C-CFTR-3UTR). Degeneration of cis-motifs was realized by direct mutagenesis using the QuickChange®II site-directed mutagenesis kit (Stratagene). All constructs were verified using direct sequencing.

microRNA Precursors and Target Site Blocker Oligonucleotides (TSB)

Pre-miR™ miRNA precursors and pre-miR™ miRNA precursor negative control were purchased from Ambion (Life Technologies). LNA™-enhanced oligonucleotides used as miRNA binding-blockers (MBBO) are named TSB, recognizing the CFTR 3'UTR overlapping the miR-101 (MBBO-1), miR-145 (MBBO-2) and miR-384 (MBBO-3) target sites were designed (EXIQON). As a control, miR-CURY LNA™ microRNA inhibitor negative control A was used (EXIQON).

Cell Culture

Human pulmonary epithelial cells (A549 and Beas-2B) were cultured as previously described (Gras D et al. J Allergy Clin Immunol 2012). Human fetal bronchial epithelial cells (HBEpiC, ScienCell, Clinisciences), isolated from a fetus at around 22 weeks of pregnancy, were primary cultured in collagen I-coated cell culture flasks in bronchial epithelial cell medium (BEpiCM, ScienCell, Clinisciences). All cells were cultured at 37° C. under 5% $CO_2$. Some studies were performed with human bronchial epithelial cell lines, the CFBE41o-(p.PHE508del1/p.PHE508del1) and the wild-type CFTR expressing, 16HBE14o-cells provided by Dr. D. C. Gruenert (San Francisco, Calif., USA). Both cell types were maintained in MEM with Earle's salts and 1-glutamine as previously described (Saint-Criq V et al. Eur J Pharmacol 2012), Cell Signal, 2012).

Nasal cells from healthy or p.Phe508del homozygous CF individuals were obtained (with the agreement N° ID-RCB 2011-A01520-41 of the French Ethical Research Committee) by inferior turbinate epithelium scratching with ASI Rhino-Pro® Curette (Arlington Scientific). Bronchial Epithelial Growth Medium (BEGM, LONZA) supplemented with antibiotics (Life Technologies) was used to promote epithelial cells initial proliferation on collagen I-coated flasks. After three weeks of monolayer growth in 37° C. 5% $CO_2$ atmosphere, cells were plated at 300,000 cells in collagen-coated 12 mm Transwell-Clear® support, 0.4 µm pore size, (Corning, Inc.). ALI (air-liquid interface) medium was used to support growth and epithelial differentiation. Top ALI medium (50:50 BEGM and DMEM 1 g/L Glucose) supplemented with specific additives (LONZA) plus Penicillin, Streptomycin and Amphotericin B (1×) (Life Technologies) was removed after confluence and bottom ALI medium was changed every 2-3 days. Experiments were performed when epithelia were well-differentiated (at least 28 days).

Transient Transfections

For Luciferase assays, cells seeded at a density of 10,000 (Beas-2B), 13,000 (A549) and 20,000 (HBEpiC) cells/100 µl of medium in 96-well plates and were transfected with 72 ng of indicated reporter vector, and 8 ng of internal control pRL-SV40 containing Renilla Luciferase (Promega) to normalize for transfection efficiency, by using Fugene®6 transfection reagent (Roche Applied Sciences). Co-transfection experiments with miRNA or TSBs (MMBOs) were performed using Interferin® transfection reagent (Polyplus, Ozyme). In addition to the reporter vector and pRL-SV40, 20 nM of microRNA precursors or 100 nM of TSBs (MMBOs) were co-transfected.

For RNA and protein studies, cells were seeded at a density of 250,000 (Beas-2B), 300,000 (A549), 500,000 (HBEpiC) cells/2 ml of medium in 6-well plates. Cells were also transfected with the same amount of miRNA precursors or TSBs (MMBOs) as defined above.

RNA Extraction, Reverse Transcription and Quantitative PCR (qPCR)

Total RNAs were extracted, reverse transcribed and amplified as previously reported (Viart V et al. Eur J Hum Genet 2012), with minor modifications. Reverse transcription was performed with either random primers or CFTR and β-actin specific primers. Quantitative PCR was carried out with 1:10 diluted cDNA and amplified with the Light-Cycler® 480 SYBR Green I Master (Roche Applied Science). Relative expression levels were calculated using the comparative DDCt method with a housekeeping gene (β-actin) expression as the endogenous control. miRNAs were purified with the miRNeasy Mini Kit and RNeasy MinElute Cleanup kit (Qiagen). Reverse transcription was performed on 40 ng of miRNA with the miRCURY LNA™ Universal cDNA synthesis kit (EXIQON) and qPCR was performed with 1:10 diluted cDNA and microRNA LNA™ primer set, specific for each miRNA (EXIQON). Relative expression levels were calculated using the comparative DDCt method with SNORD44 and SNORD48 small nucleolar RNA as the endogenous controls. To validate key microarray results (miRNA and RNA profiling), RT-qPCR was performed as explained above.

Reporter Assay

Cells were harvested 48 h after transfection, and the activity of Firefly Luciferase and Renilla Luciferase was measured using the Dual-Glo® Luciferase Assay System (Promega).

Western Blot

Whole proteins were directly extracted using 1× Laemmli buffer. Proteins were separated on 7% or 10% SDS-PAGE gels and transferred to PVDF membrane (Westran® Clear Signal Whatman®, Dutsher SAS). The proteins were detected using 1:400 diluted anti-CFTR (clone MM13-4, Millipore) in 5% skim milk. The protein levels of Lamin A/C (1:10,000, Sigma Aldrich) were assayed for internal control of protein loading. Following 1 h of incubation with the anti-mouse secondary antibodies, proteins were revealed by chemiluminescence.

CFTR Activity

The activity of CFTR protein was assessed by I-quenching of halide-sensitive YFP as previously described (Saint-Criq V et al. Eur J Pharmacol 2012) using Premo Halide sensor technology (Invitrogen, Villebon sur Yvette, France). Forty hours following MBBO treatment, CFTR conductance was stimulated by an agonist mixture (forskolin, 3-isobutyl-1methylxanthine, apigenin). After 10 min, the 96-well plates were transferred to a plate reader for fluorescence assay. Each well was assayed individually for CFTR-mediated I⁻ efflux by recording fluorescence continuously (400 ms/point) for 2 s (base line), then 50 µl of a 140 mM I⁻ solution.

Statistical Analysis

For Luciferase and RT-qPCR assays, experiments were performed at least three times with samples analyzed at least in triplicate and paired comparisons were made using Student's t-test using InStat (GraphPad Software, version 3.0, Instat 3 folder). Data were expressed as the mean±SE and were considered statistically significant at $p<0.0001$. For assessing MBBO impact, statistical analyses were made using Wilcoxon statistics with R software that generates box plots with significances.

Results

A Complex Pattern of Cis and Trans-Acting Elements in the 3'UTR is Involved in the Regulation of the Temporal Expression of CFTR Gene To evaluate the effect of the 3'UTR on the post-transcriptional regulation of the CFTR gene, the inventors transfected adult cell lines and primary fetal HBEpiC with a reporter vector, either with or without the CFTR 3'UTR. The results show that the 3'UTR of the CFTR gene induced strong repression of Luciferase activity, in all cell-types, indicating that this region contains cis-repressive elements. Using the bioinformatic tool AREsite (http://rna.tbi.univie.ac.at/cgi-bin/AREsite.cgi), the inventors identified four putative AU-rich elements (ARE) in the 3'UTR of the CFTR gene: ARE-4816, ARE-5533, ARE-5698 and ARE-6074. These sites are additional to those previously described (Baudouin-Legros M et al. AJPCP, 2005), that the inventors renamed ARE-4585, ARE-4760 and ARE-4891 according to their nucleotide position. The inventors next evaluated the degeneration of these motifs using reporter assays. Only one motif, ARE-4760, appeared to be implicated in mRNA stabilization, as its degeneration was associated with a decrease in Luciferase activity. Although ARE-4585, ARE-5533, ARE-5698 and ARE-6074 appeared to be involved in destabilization in A549 and Beas-2B, they had no effect in HBEpiC. The strongest effect was obtained using ARE-5698, identified in silico as the most conserved ARE motif in the CFTR 3'UTR. Other cis-acting elements might explain the repressive activity of the 3'UTR of CFTR in adult cell lines. Computational predictions using TargetScan (http://www.targetscan.org/), Pictar (http://pictar.mdc-berlin.de), miRanda (http://www.microrna.org/microrna/home.do) and miRDB (http://mirdb.org/miRDB/) detect thirteen putative miRNA binding motifs in the CFTR 3'UTR. Of the eight miRNAs previously studied, miR-145 has been involved in the regulation of CFTR expression in colonic and pancreatic cell lines (Gillen A E et al. Biochem J, 2011).

The inventors then assessed the role of miRNAs in the post-transcriptional control of CFTR in pulmonary cells by using Luciferase reporter assays after transfection with precursors. MiR-665, miR-383 and miR-1290 did not induce an effect in any cell type, whereas miR-600 affected Luciferase activity in all cells studied. MiR-505, miR-943, miR-377, miR-145, miR-384, miR-101 and miR-1246 only induced a decrease in Luciferase activity in A549 and/or Beas-2B, but not in HBEpiC. To confirm the importance of the cognate cis-elements, the inventors degenerated the motif for the binding of both miR-505 and miR-101 resulting in the greatest effect on CFTR post-transcriptional regulation. Two such degenerated sites were associated with a modest increase of Luciferase activity, but only in adult pulmonary cells. The inventors next validated the repressive effect of miR-101 on post-transcriptional regulation of the CFTR gene in adult pulmonary cells. Overexpression of the miR-101 precursor was controlled.

Previous studies have demonstrated that miRNA-mediated regulation might require the presence of an ARE sequence (Jing Q et al. Cell, 2005; Sun G et al NAR, 2010; Glorian V et al. Cell Death Differ, 2011). Both the miR-101 and miR-600 binding sites overlap the ARE-6074 motif and the miR-384 binding site overlaps the ARE-5698 motif. To investigate whether the impact of the miRNAs binding is dependent on the integrity of ARE motifs, we performed co-transfection assays with the miR-101, miR-600 and miR-384 precursors and the constructs containing the wild-type or degenerated CFTR 3'UTR. Only miR-101 lost its repressive effect on Luciferase activity following both the degeneration of the CFTR sequence homologous to its seed region and abrogation of ARE-6074. Degeneration of ARE-6074 and ARE-5698 did not affect the activity of miR-600 and miR-384, respectively.

These data demonstrate the implication of miRNAs in the tightly controlled developmental regulation of CFTR expression and more particularly that miR-101 directly acts on its cognate site in combination with an overlapping ARE motif From Identifying Crucial Regulators to Testing New Potential Therapeutic Tools for Cystic Fibrosis The region encompassing the miR-101 binding site and ARE-6074 is critical to the regulatory action of miR-101. Thus, miRNA binding-blocker oligonucleotides (MBBO) were designed to prevent the binding of several miRNAs including miR-101, miR-600, miR-145 and miR-384 to the 3'UTR of the CFTR gene. Use of these MBBOs, co-transfected with the reporter gene, led to a 1.5- to 6-fold overexpression of Luciferase activity in different cell lines (FIG. 1A). The increase in level of endogenous CFTR by the MBBO-1 was confirmed in pulmonary cells (FIG. 1B).

Next, in order to evaluate the effect of the MBBOs in vivo, the inventors introduced MBBOs into reconstituted ALI epithelium cultured from human nasal cells from control individuals and p.Phe508del homozygous CF patients. Control oligonucleotide, MBBO-1 or MBBO-2 was added to the apical side of primary nasal cells without transfection reagent. After 2 h at 37° C., the apical medium was removed to restore the air-liquid interface. Application was repeated every 2 days with either freshly prepared control oligonucleotide or MBBOs. Use of MBBO-1 induced a 2- to 6-fold increase of the endogenous CFTR transcript level in controls (FIG. 1C) and a 2- to 3-fold increase in patients (FIG. 1D), and no marked improvement with a repeated number of incorporation of the MBBO-1. FIG. 1E represents the box plot of the MBBO-1, MBBO-2 and MBBO-3 24 h post-treatment in ALI epithelium cultured from p.Phe508del homozygous CF patients (FIG. 1E). Immunoblot assays also revealed a stronger expression of CFTR proteins in epithelium treated with both the MBBO-1, MBBO-2 and MBBO-3 in ALI epithelium cultured from CF patients (FIG. 1F). Functional assays showed the absence of CFTR-dependent anion transport in CFBE41o-cells compared to wild-type 16HBEo-(FIG. 1G). In contrast, a significant increase in level of anion transport was observed in CF cells treated with MBBO compared to the non-treated CFBE in accordance with the functional CFTR amount detected by immunoblot (FIG. 1H).

These data support the importance of the regions encompassing the miR-101 and miR-145 binding sites in regulation of the CFTR gene in native cells and offer a new insight for CF therapeutics.

Discussion

Herein, the inventors showed that miRNAs, including miR-101 and miR-145, negatively regulate the level of CFTR transcripts in adult lung cells whilst having no effect in fetal lung cells. Interestingly, in addition to its specific role in mature lung cells, miR-101 has recently been described as not altering CFTR mRNA stability in pancreatic cell lines Gillen A E et al. Biochem J, 2011) but inducing a decrease of Luciferase activity in an embryonic kidney cell line (Mergiorni F et al Plos One, 2011), suggesting a potential role as a tissue-specific factor. The inventors demonstrated the implication of miRNAs, in the tightly controlled developmental regulation of CFTR expression and more particularly, that miR-101 acts on its cognate site in combination with an overlapping ARE motif.

Herein, the inventors also demonstrated the benefit of characterizing regulatory factors to identify novel therapeutic targets. Additionally, early studies indicated that complementation of as few as 6-10% CFTR transcripts generate enough CFTR levels to maintain normal chloride transport in the epithelia (Sinn P L et al. Hum Mol Genet, 2011). These data are supported by findings that the presence of a naturally occurring sequence variation in the CFTR promoter, in cis of a severe mutation, which increases transcription, can allow enough CFTR protein to reach apical membrane cells in order to restore partial function, thus inducing a moderate CF phenotype (Romey M C et al. JBC, 2000). More recently, increasing the amount of p.Phe508del CFTR protein has been associated with an activated p.Phe508del CFTR channel activity (Hutt D M et al. Nat Chem Biol, 2010). A recent work demonstrates that use of miR-138 mimic as potential therapeutic tool, restores CFTR-Phe508del and a functional Cl-transport (Ramachandran S et al. PNAS, 2012). As miR-138 targets SIN3, a highly conserved transcriptional repressor regulating many genes, the authors underlined that use of miR-138 mimic may have undesirable effect (Ramachandran S et al. PNAS, 2012). Herein, the inventors tested a new putative therapeutic tool that specifically targets the CFTR gene. Focusing on miR-101 and miR-145, the inventors designed MBBO oligonucleotides, recognizing their binding sites in the CFTR 3'UTR. This blockage led to the correction of the CFTR channel activity through increase of mRNA and protein levels in CF patients with the most severe mutation, the p.Phe508del in homozygous. As miR-101 and miR-145 knock-down is associated with the dysregulation of epigenetic pathways resulting in cancer progression (Varambally S et al. Science, 2008) and lung cancer (Guan P et al. J Exp Clin Cancer Res, 2012), inventor's approach of blocking their binding to their cognate CFTR mRNA motif may have therapeutic benefits by stabilizing CFTR transcripts, ultimately providing enough functional proteins to improve CF patients phenotype.

Example 2

Material & Methods

```
TSB Oligonucleotides sequences
TSB1:         GTT GGT ACT TCT GTA ATA

TSB2:         ACC TTA CTT ATA TCT CAA
```

In Silico Analysis

First, the CFTR variants was analysed using Human Splicing Finder 2.4.1 (http://www.umd.be/HSF/HSF.html), including two different calculation algorithms (HSF and MaxEnt) and NNSplice (http://www.fruitfly.org/seq_tools/splice.html; Splice Site Prediction by Neural Network or SSPNN). We assumed that aberrant splicing could occur when a de novo splice site (ss) was predicted or when the score of a sub-optimal pre-existing ss was dramatically increased in the mutated sequence. We also evaluated wild type (wt) and mutated sequences using the SpliceAid 2 database (http://193.206.120.249/splicing_tissue.html).

Second, we evaluated the conservation of the nucleotide position affected by a substitution in a set of selected mammalian orthologues. We first aligned the human genomic sequence of CFTR (NC_000007.13) with nine vertebrate orthologues from Ensembl using the MUSCLE3.7 algorithm available at www.phylogeny.fr. Results, shown as percentages of the wt and variant nucleotides, were obtained by analysing the multiple alignments with the Jalview software (http://www.jalview.org/). A broader analysis with visualization of the multiple alignments of 19 CFTR orthologues, including human CFTR, was obtained from UCSC using the Multiz Alignments tool. The wt nucleotide was considered as highly conserved when its frequency was higher than 90%, intermediately conserved between 50 and 90% and poorly conserved when its frequency was lower than 50% and/or when the mutated nucleotide was found with a frequency of at least 10%.

Splicing Reporter Constructs

The impact of the newly discovered variant on splicing was tested using the pSPL3 exon-trapping vector (kindly provided by Dr I. Bottillo). We amplified the CFTR sequence of interest (632 bp) in intron 12 (legacy nomenclature: intron 11) using the patient's genomic DNA (diluted to 5 ng/μl) and the High Fidelity Phusion® polymerase (Finnzymes, Espoo, Finland). The amplicon was inserted in pSPL3 between the XhoI and NheI restriction sites using the T4 DNA ligase High Concentration (Invitrogen, Villebon sur Yvette, France) according to the manufacturer's instructions. In addition to the wild-type (wt) and mutated (c.1680-883A>G) minigenes, two other CFTR minigenes were generated carrying the SNP c.1680-870T>A (negative control for aberrant splicing) or the splicing mutation c.1680-886A>G (1811+1.6 kb A>G) (positive control for aberrant splicing). All primer sequences are available upon request. The sequences of the minigene constructs were verified by Sanger sequencing.

Cell Culture, Transfection and Target Site Blocker (TSB) Treatment

Human bronchial BEAS-2B cells were cultured as previously described (Rene C et al. *Cell. Mol. Life Sci.* 2010). Twenty-four hours before transfection, cells were plated in six-well plates and, once at about 80% confluence, transiently transfected with 1.5 μg of each minigene construct using the PolyFect® transfection reagent (Qiagen, Courtaboeuf, France). Cells were harvested after 48 hours for transcript analysis. For TSB (TSB1 and TSB2) treatment, cells were co-transfected with the CFTR minigene constructs and 25 nM, 50 nM, 100 nM or 1 μM TSB using the Interferin® transfection reagent (Polyplus, Ozyme, Illkirch, France).

Transcript Analysis

Total RNA was extracted from BEAS-2B cells using the RNeasy Plus kit (Qiagen). At least, two independent transfections were carried out for all experimental conditions. Impact on splicing was tested as previously reported. The RT-PCR products were also sequenced using the Big Dye Terminator v1.1 Cycle Sequencing Kit (Applied Biosystems) on an ABI-3130XL Genetic Analyzer. The relative amount of each CFTR splicing product was determined by measuring the peak area (evaluated by the GeneMapper software) and dividing it by the sum of all peak areas detected in the same PCR reaction.

Total RNA was extracted from the patient's nasal cells and from two non-CF controls using the RNeasy Plus kit (Qiagen). Reverse transcription was produced from 500 ng of total RNA with the MMLV-RT (Invitrogen). One μL of each RT-PCR was used for PCR amplification with primers encompassing intron 12 (f11-r13) and specific primers pairs amplifying pseudoexon, PE (f11-rPE).

Results

Identification of a New Putative Disease-Causing Mutation

To explore the effect of the c.1680-883A>G variation (located in intron 12; chromosome location: 117,229,524; hg19), donor (5'ss) and acceptor site (3'ss) in silico predictions were generated for the mutated sequence. The mutation generated a new, high-score 5' ss in intron 12, suggesting that this site could be used for alternative splicing. The newly identified putative disease-causing mutation c.1680-883A>G is three nucleotides away from a well-known splice mutation [c.1680-886A>G (1811+1,6 kbA>G) Chillon M et al. Am J Hum Genet, 1995] that creates a donor site causing the inclusion of a PE in mature transcripts. In other respects, the mutation was tested in 200 control chromosomes by Sanger sequencing analysis and was not found.

Confirmation of the c.1680-883A>G Intronic Mutation Using a Splicing Reporter Assay and in Nasal Cells of a Patient We next used a splicing reporter assay to test the impact of the c.1680-883A>G variant on splicing. When BEAS-2B cells were transfected with the minigene carrying the c.1680-886A>G variant (used as positive control), which causes the inclusion of an intronic sequence of 49 bp (cryptic exon inclusion, CEI), aberrantly-spliced transcripts were approximately 90-95% of the total (wild-type+aberrantly-spliced) CFTR mRNA. Conversely, transfection of the minigene carrying the neutral variant c.1680-870T>A (negative control) did not have any effect on splicing. Finally, transfection of the minigene carrying the newly identified c.1680-883A>G mutation led to activation of a pseudoexon (PE) resulting in the inclusion of an additional sequence of 53 bp, as shown by Sanger sequencing, and complete loss of wt CFTR transcripts.

We next checked if this mutation induced the sequence retention in nasal cells from the CF patient included in the family trio analysis. Thus, we confirmed that the patient harboured a PE inclusion of 53 bp in intron 12 by PCR amplification compared to controls using non-specific and specific primers pairs to the PE (f11-r13 and f11-rPE, respectively).

Correction of CFTR aberrant splicing by Using Target Site Blockers (TSB1 and TSB2)

We designed anti-sense oligonucleotides (TSB1 and TSB2) that block access to the 3'ss (acceptor site) and 5'ss (donor site) respectively, in order to correct aberrant splicing caused by the c.1680-883A>G and c.1680-886A>G mutations. To determine the effect of TSB concentration on aberrant splicing, human bronchial BEAS-2B cells were co-transfected with the minigenes harbouring the two mutations and four different TSB concentrations (25 nM, 50 nM, 100 nM, 1 µM) for 24 h. TSB1, which targets the 3'ss (acceptor site), had a marked corrective effect at low concentration (50 nM) on aberrant splicing caused by the c.1680-883A>G and c.1680-886A>G mutations (FIG. 2A, upper and lower panel, respectively). TSB1 specificity was confirmed by using a TSB control (CTL). The efficiency of wt splicing restoration was quantified by fragment analysis PCR (FIG. 2B). We next performed time course experiments by transfecting 50 nM TSB1 and harvesting cells after 24 h, 48 h and 72 h. A marked effect was evident already after 24 h (FIG. 2C). Specifically, quantification showed that the percentage of aberrantly spliced transcripts (containing the cryptic exon) was reduced to 45% (c.1680-883A>G) and to 30% (c.1680-886A>G) of the total CFTR mRNA (wild-type+aberrantly-spliced transcripts). Thus, transfection of 50 nM TSB1 for 24 h induced a restoration of 55% and 70% of normal CFTR mRNA, respectively (FIG. 2D). Finally, we assessed the duration of action of both TSB (TSB1 and TSB2) in BEAS-2B cells and found that they had a strong effect on splicing up to 72 h after washing off the transfection medium (16 h incubation) (FIG. 2E). Partial restoration of correctly-spliced CFTR mRNA induced by TSB1 (24 h at 100 nM) was confirmed in primary nasal cultures obtained from a control individu (FIG. 2F). TSB2 required a higher concentration for acting on splicing (FIG. 3).

Discussion

Among the 1976 reported CFTR mutations, 228 (11.54%) are believed to affect pre-mRNA splicing (www.genet.sickkids.on.ca/). Most splicing mutations disrupt the canonical splice-site sequences, completely abolishing exon recognition and/or leading to a nearly complete absence of correctly spliced transcripts. Currently, 2 to 5% of CF mutations remain unknown and are probably deeply located in introns, inducing aberrant splicing events. Functional analysis, minigene splicing assay and PCR on nasal cells from a CF patient carrying c.1680-883A>G, showed that this deep intronic mutation generated a new, high-score 5' ss (donor site) in intron 12 that is involved in PE inclusion. Interestingly, this mutation is close to another previously identified deep intronic mutation, the c.1680-886A>G, that also induces pseudoexonPE inclusion, suggesting that this intronic region may be prone to mutation. The c.1680-886A>G mutation occurs with a frequency of 3.4% in the South-West part of Europe and of 0.2% in France (Federici S, 2001). Conversely, c.1680-883A>G has never been described before, though here identified in three unrelated patients.

The final objective of this work was the design of antisense oligonucleotides for CF treatment. Indeed, PE exclusion by antisense modification of pre-mRNA splicing represents a type of personalized genetic medicine. The development of oligonucleotides that block access to a target site (Target site blockers, TSB) offers new treatment opportunities for other genetic disorders (Webb T R et al. Hum Mol Genet 2012, Nuzzo F et al. Blood, 2013). Here, we used this approach to correct the aberrant splicing caused by deep intronic mutations in the CFTR gene (c.1680-883A>G and c.1680-886A>G). TSB effect on aberrant splicing correction in bronchial BEAS-2B cells was rapid and maintained over time, suggesting that TSBs could be a therapeutic tool in patients with CF who have deep intronic mutations in the CFTR gene because they restore normal transcripts. For patients with CF, these data are particularly interesting because the c.1680-886A>G mutation is the fourth most frequent in South-West Europe (3.4%) and the threshold of functional mRNA and subsequently of CFTR protein required for normal functions is very low, having been estimated at 5% (Ramalho A S et al. Am J Respir Cell Mol Biol 2002). It would be interesting, if possible, to test these TSBs in airway cells from patients with CF harbouring both mutations tested in this work and also to assess TSBs for other intronic splicing mutations in CFTR.

REFERENCES

Throughout this application, various references describe the state of the art to which this invention pertains. The disclosures of these references are hereby incorporated by reference into the present disclosure.

Baudouin-Legros M, Hinzpeter A, Jaulmes A, Brouillard F, Costes B, et al. (2005) Cell-specific posttranscriptional regulation of CFTR gene expression via influence of MAPK cascades on 3'UTR part of transcripts. Am J Physiol Cell Physiol 289: C1240-1250.

Boucher R C. Cystic fibrosis: a disease of vulnerability to airway surface dehydration. Trends Mol Med. 2007 June; 13(6):231-40.

Chillon M, Dork T, Casals T, et al. A novel donor splice site in intron 11 of the CFTR gene, created by mutation 1811+1.6 kbA→G, produces a new exon: high frequency in Spanish cystic fibrosis chromosomes and association with severe phenotype. *Am J Hum Genet* 1995; 56:623-9

Farrell P M, Rosenstein B J, White T B, Accurso F J, Castellani C, Cutting G R, Durie P R, Legrys V A, Massie J, Parad R B, Rock M J, Campbell P W 3rd; Cystic Fibrosis Foundation. Guidelines for diagnosis of cystic fibrosis in newborns through older adults: Cystic Fibrosis Foundation consensus report. J Pediatr. 2008 August; 153(2):S4-S14.

Federici S, Iron A, Reboul M P, et al. [CFTR gene analyis in 207 patients with cystic fibrosis in southwest France: high frequency of N1303K and 1811+1.6 bA>G mutations]. *Archives de pediatric: organe officiel de la Societe francaise de pediatrie* 2001; 8:150-7.

Gillen A E, Gosalia N, Leir S H, Harris A (2011) MicroRNA regulation of expression of the cystic fibrosis transmembrane conductance regulator gene. Biochem J 438: 25-32. Jing Q, Huang S, Guth S, Zarubin T, Motoyama A, et al. (2005) Involvement of microRNA in AU-rich element-mediated mRNA instability. Cell 120: 623-634.

Glorian V, Maillot G, Poles S, Iacovoni J S, Favre G, et al. (2011) HuR-dependent loading of miRNA RISC to the mRNA encoding the Ras-related small GTPase RhoB controls its translation during UV-induced apoptosis. Cell Death Differ 18: 1692-1701.

Gras D, Bourdin A, Vachier I, et al. An ex vivo model of severe asthma using reconstituted human bronchial epithelium. J Allergy Clin Immunol 2012; 129: 1259-1266.

Guan P, Yin Z, Li X, Wu W, Zhou B (2012) Meta-analysis of human lung cancer microRNA expression profiling studies comparing cancer tissues with normal tissues. J Exp Clin Cancer Res 31: 54.

Hutt D M, Herman D, Rodrigues A P, Noel S, Pilewski J M, Matteson J, Hoch B, Kellner W, Kelly J W, Schmidt A, Thomas P J, Matsumura Y, Skach W R, Gentzsch M, Riordan J R, Sorscher E J, Okiyoneda T, Yates J R 3rd, Lukacs G L, Frizzell R A, Manning G, Gottesfeld J M, Balch W E. Reduced histone deacetylase 7 activity restores function to misfolded CFTR in cystic fibrosis. Nat Chem Biol. 2010 January; 6(1):25-33.

Martinez N J, Walhout A J (2009) The interplay between transcription factors and microRNAs in genome-scale regulatory networks. Bioessays 31: 435-445.

Megiorni F, Cialfi S, Dominici C, Quattrucci S, Pizzuti A (2011) Synergistic post-transcriptional regulation of the Cystic Fibrosis Transmembrane conductance Regulator (CFTR) by miR-101 and miR-494 specific binding. PLoS One 6: e26601.

Nuzzo F, Radu C, Baralle M, et al. Antisense-based RNA therapy of factor V deficiency: in vitro and ex vivo rescue of a F5 deep-intronic splicing mutation. Blood 2013; 122: 3825-31.

Oglesby I K, Chotirmall S H, McElvaney N G, Greene C M (2013) Regulation of cystic fibrosis transmembrane conductance regulator by microRNA-145, -223, and -494 is altered in DeltaF508 cystic fibrosis airway epithelium. J Immunol 190: 3354-3362.

Ramachandran S, Karp P H, Jiang P, Ostedgaard L S, Walz A E, et al. (2012) A microRNA network regulates expression and biosynthesis of wild-type and DeltaF508 mutant cystic fibrosis transmembrane conductance regulator. Proc Natl Acad Sci USA 109: 13362-13367.

Ramachandran S, Karp P H, Osterhaus S R, Jiang P, Wohlford-Lenane C, et al. (2013) Post-transcriptional Regulation of CFTR Expression and Function by MicroRNAs. Am J Respir Cell Mol Biol.

Ramalho A S, Beck S, Meyer M, Penque D, Cutting G R and Amaral M D. Five percent of normal cystic fibrosis transmembrane conductance regulator mRNA ameliorates the severity of pulmonary disease in cystic fibrosis. Am J Respir Cell Mol Biol 2002; 27:619-27.

Ramsey B W, Davies J, McElvaney N G, Tullis E, Bell S C, Dřevínek P, Griese M, McKone E F, Wainwright C E, Konstan M W, Moss R, Ratjen F, Sermet-Gaudelus I, Rowe S M, Dong Q, Rodriguez S, Yen K, Ordoñez C, Elborn J S; VX08-770-102 Study Group. A CFTR potentiator in patients with cystic fibrosis and the G551D mutation. N Engl J Med. 2011 Nov. 3; 365(18):1663-72.

Rene C, Lopez E, Claustres M, Taulan M and Romey-Chatelain M C. NF-E2-related factor 2, a key inducer of antioxidant defenses, negatively regulates the CFTR transcription. *Cell. Mol. Life Sci.* 2010; 67:2297-2309.

Romey M C, Pallares-Ruiz N, Mange A, Mettling C, Peytavi R, et al. (2000) A naturally occurring sequence variation that creates a YY1 element is associated with increased cystic fibrosis transmembrane conductance regulator gene expression. J Biol Chem 275: 3561-3567.

Saint-Criq V, Ruffin M, Rebeyrol C, et al. Azithromycin fails to reduce inflammation in cystic fibrosis airway epithelial cells. Eur J Pharmacol 2012; 674: 1-6.

Sawicki G S, Sellers D E, Robinson W M. High treatment burden in adults with cystic fibrosis: challenges to disease self-management. J Cyst Fibros. 2009 March; 8(2):91-6.

Shalgi R, Brosh R, Oren M, Pilpel Y, Rotter V (2009) Coupling transcriptional and post-transcriptional miRNA regulation in the control of cell fate. Aging (Albany N.Y.) 1: 762-770.

Sinn P L, Anthony R M, McCray P B, Jr. (2011) Genetic therapies for cystic fibrosis lung disease. Hum Mol Genet 20: R79-86.

Sun G, Li H, Rossi J J (2010) Sequence context outside the target region influences the effectiveness of miR-223 target sites in the RhoB 3'UTR. Nucleic Acids Res 38: 239-252.

Van Goor F, Hadida S, Grootenhuis P D, Burton B, Stack J H, Straley K S, Decker C J, Miller M, McCartney J, Olson E R, Wine J J, Frizzell R A, Ashlock M, Negulescu P A. Correction of the F508del-CFTR protein processing defect in vitro by the investigational drug VX-809. Proc Natl Acad Sci USA. 2011 Nov. 15; 108(46):18843-8.

Verkman A S, Galietta L J. Chloride channels as drug targets. Nat Rev Drug Discov. 2009 February; 8(2):153-71.

Varambally S, Cao Q, Mani R S, Shankar S, Wang X, et al. (2008) Genomic loss of microRNA-101 leads to overexpression of histone methyltransferase EZH2 in cancer. Science 322: 1695-1699.

Viart V, Des Georges M, Claustres M, et al. Functional analysis of a promoter variant identified in the CFTR gene in cis of a frameshift mutation. Eur J Hum Genet 2012; 20: 180-184.

Webb T R, Parfitt D A, Gardner J C, et al. Deep intronic mutation in OFD1, identified by targeted genomic next-generation sequencing, causes a severe form of X-linked retinitis pigmentosa (RP23). *Hum Mol Genet* 2012; 21:3647-54.

The invention claimed is:

1. A method for preventing or treating cystic fibrosis transmembrane conductance regulator gene (CFTR)-related disease in a subject in need thereof comprising the step of administering to said subject an oligonucleotide comprising a nucleic acid sequence selected from the group consisting of SEQ ID NO: 1, SEQ ID NO: 2, SEQ ID NO: 3, SEQ ID NO: 4 and SEQ ID NO: 5, wherein administration of the oligonucleotide results in preventing or treating the CFTR-related disease.

2. The method of claim 1, wherein said CFTR-related disease is cystic fibrosis.

3. The method of claim 1, wherein the oligonucleotide is administered in combination with one or more anti-CFTR-related disease agents.

4. The method of claim 2, wherein the oligonucleotide is administered in combination with one or more anti-cystic fibrosis agents.

5. The method according to claim 3 wherein said one or more anti-CFTR-related disease agents is selected from the group consisting of ivacaftor VX-770, VX-661 and VX-809.

6. The method according to claim 4 wherein said anti-cystic fibrosis agent is selected from the group consisting of ivacaftor VX-770, VX-661 and VX-809.

* * * * *

SEQUENCE LISTING

```
<160> NUMBER OF SEQ ID NOS: 5

<210> SEQ ID NO 1
<211> LENGTH: 22
<212> TYPE: DNA
<213> ORGANISM: Artificial
<220> FEATURE:
<223> OTHER INFORMATION: TSB MBBO-1

<400> SEQUENCE: 1
agtgatattt tcttacagta at                                              22

<210> SEQ ID NO 2
<211> LENGTH: 26
<212> TYPE: DNA
<213> ORGANISM: Artificial
<220> FEATURE:
<223> OTHER INFORMATION: TSB MBBO-2
```

```
<400> SEQUENCE: 2
ataaaccgct gaagtttcca gttatc                                        26

<210> SEQ ID NO 3
<211> LENGTH: 28
<212> TYPE: DNA
<213> ORGANISM: Artificial
<220> FEATURE:
<223> OTHER INFORMATION: TSB MBBO-3

<400> SEQUENCE: 3
acattattaa aataaatatt tcctagag                                      28

<210> SEQ ID NO 4
<211> LENGTH: 18
<212> TYPE: DNA
<213> ORGANISM: Artificial
<220> FEATURE:
<223> OTHER INFORMATION: TSB TSB1

<400> SEQUENCE: 4
gttggtactt ctgtaata                                                 18

<210> SEQ ID NO 5
<211> LENGTH: 18
<212> TYPE: DNA
<213> ORGANISM: Artificial
<220> FEATURE:
<223> OTHER INFORMATION: TSB TSB2

<400> SEQUENCE: 5
accttactta tatctcaa                                                 18
```